(12) United States Patent
Casara et al.

(10) Patent No.: US 6,846,833 B2
(45) Date of Patent: Jan. 25, 2005

(54) VITRONECTIN RECEPTOR ANTAGONIST BICYCLIC COMPOUNDS, PREPARATION METHOD AND COMPOSITIONS CONTAINING SAME

(75) Inventors: Patrick Casara, Villennes sur Seine (FR); Françoise Perron-Sierra, Paris (FR); Ghanem Atassi, Cabrials (FR); Gordon Tucker, Paris (FR); Dominique Saint-Dizier, Rueil Malmaison (FR)

(73) Assignee: Les Laboratoires Servier, Courbevoie (FR)

( * ) Notice: Subject to any disclaimer, the term of this patent is extended or adjusted under 35 U.S.C. 154(b) by 50 days.

(21) Appl. No.: 10/220,755

(22) PCT Filed: Mar. 6, 2001

(86) PCT No.: PCT/FR01/00650

§ 371 (c)(1),
(2), (4) Date: Sep. 3, 2002

(87) PCT Pub. No.: WO01/79172

PCT Pub. Date: Oct. 25, 2001

(65) Prior Publication Data

US 2003/0229109 A1 Dec. 11, 2003

(30) Foreign Application Priority Data

Mar. 7, 2000 (FR) ............................................. 00 02902

(51) Int. Cl.[7] ...................... A61K 31/44; C07D 267/02; C07D 239/02; C07D 211/72; C07D 235/22
(52) U.S. Cl. ...................... 514/300; 514/275; 514/396; 514/398; 514/352; 540/490; 544/269; 544/323; 546/122; 546/123; 546/312; 548/307.4
(58) Field of Search ...................... 540/490; 544/269, 544/323; 546/122, 123, 312; 514/300, 275, 396, 398, 352; 548/307.4

(56) References Cited

U.S. PATENT DOCUMENTS 6,239,138 B1 * 5/2001 Ku ............................... 514/277
6,403,578 B1 * 6/2002 Bondinell et al. ........... 514/221

FOREIGN PATENT DOCUMENTS

| FR | 2806082 | * | 9/2001 |
| WO | WO 96/00730 | * | 1/1996 |
| WO | WO 96/06087 | * | 2/1996 |
| WO | WO 98/14192 | * | 4/1998 |
| WO | WO 98/30542 | * | 7/1998 |
| WO | WO 99/05107 | * | 2/1999 |
| WO | WO 99/15508 | * | 4/1999 |

* cited by examiner

Primary Examiner—D. Margaret Seaman
(74) Attorney, Agent, or Firm—The Firm of Hueschen and Sage

(57) ABSTRACT

Compounds of formula (1):

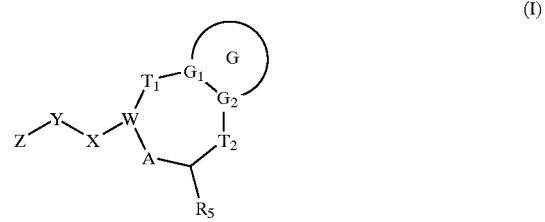

wherein:

G represents an optionally substituted phenyl or optionally substituted heterocycle, $G_1$ and $G_2$ being N or C, $T_1$ represents —$CH_2$—$CH_2$—, —CH=CH— or =CH—$CH_2$—, and $T_2$ is a bond, or $T_1$ represents —$CH_2$— or =CH— and $T_2$ is —$CH_2$—, =CH—,

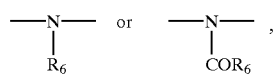

$R_5$ represents —$(CH_2)_m$—$COOR_6$, $R_6$ and $R_{6'}$ represent hydrogen, alkyl, optionally substituted aryl or optionally substituted arylalkyl, A represents —CO—, —$CH_2$—, =CH— or —CH= and W represents —CH—, =C— or —C=, or A represents —CO— or —$CH_2$— and W represents N, X represents —CO—$X_1$—, —CO—$NR_6$—$X_1$—, —$NR_6$—CO—$X_1$—, —O—$X_1$—, —$SO_2$—$NR_6$—$X_1$— or —$S(O)_n$—$X_1$—, Y represents —$Y_1$—, —$Y_2$—$Y_1$— or —$Y_1$—$Y_2$—$Y_1$—, $Y_1$ being an alkylene, alkenylene or alkynylene, and $Y_2$ being an arylene, heteroarylene, cycloalkylene or heterocycloalkylene, Z represents —$Z_1$—, —$Z_{10}$—$NR_6$—, and —$Z_{10}$—$NR_6$—CO—, $Z_1$ being a heteroaryl, heterocycloalkyl, heteroarylalkyl, heterocycloalkylalkyl, fused arylheteroaryl, fused arylheterocycloalkyl, fused heteroarylheterocycloalkyl, fused heterocycloalkylheteroaryl or fused heteroarylheteroaryl, each of which is optionally substituted, or a group,

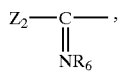

$Z_2$—$NR_6$ or $Z_2$—$NR_6$—CO, $Z_2$ being a group $Z_1$, alkyl or heteroalkyl, and $Z_{10}$ represents $Z_1$ or an alkyl, its enantiomers, diastereoisomers, and addition salts thereof with a pharmaceutically acceptable acid or base, and medicinal products containing the same which are useful as vitronectin receptor antagonists.

24 Claims, No Drawings

VITRONECTIN RECEPTOR ANTAGONIST BICYCLIC COMPOUNDS, PREPARATION METHOD AND COMPOSITIONS CONTAINING SAME

The present invention relates to new bicyclic vitronectin receptor antagonist compounds, to a process for their preparation and to pharmaceutical compositions containing them.

Integrins are a family of transmembrane glycoproteins identified initially for their dynamic characteristics of cell adhesion and cell migration and providing a mechanical bond between the extracellular matrix and other surface adhesion molecules and the cytoskeleton. Their capacity to transmit an intracellular signal directly was described subsequently. Those two properties of coupling agent and receptor are employed by cells during embryonic development and during a large number of physiological processes (Cell., 1992, 69, 11–25; Endocrine Reviews, 1996, 17, 207–220; Cell. Mol. Life Sci., 1998, 54, 514–526).

An integrin consists of two distinct chains, alpha and beta, bonded to each other in a non-covalent manner. At least sixteen alpha chains and eight beta chains have been identified, their combination allowing the creation of a vast repertoire of possibilities. Of those, only about twenty integrins have been described. The type of combination of the sub-units also dictates the repertoire of the identified extracellular ligands. The peptide sequence Arg-Gly-Asp (RGD) is often recognised by intregrins and is present in a large number of ligands (fibronectin, vitronectin, fibrinogen, collagen, . . . ), but other recognition sites have been described. An integrin can exist in a form incapable of binding its ligands and will therefore require activation by the convergence of various intracellular signals in order to be come functional (Cell., loc.cit; J. Clin. Invest., 1997, 99, 2302–2306).

If integrins are able to serve as an access route for viral, bacterial or parasitic cell infections, the deregulation of their expression or of their activation will be associated with a large number of pathologies, including, for example, cardiovascular disease, inflammatory disorders, cancer, osteoporosis, rheumatoid arthritis, psoriasis and retinopathy. Integrins take part in the development of such pathologies by acting on the adhesion and migration of cells, on the regulation of cell differentiation, survival and proliferation, and on the transmission of various intracellular signals (Ann. Rep. In Med. Chem., 1996, 31 191–200).

$\alpha_v\beta_3$ integrin, one of the vitronectin receptors but binding also to fibronectin, fibrinogen and thrombospondin, has been implicated more especially in three pathological events: the migration of smooth muscle cells in neointima, during atherosclerosis and restenosis following angioplasty, to the surface of osteoclasts during bone resorption, and during phases of angiogenesis on endothelial cells (Cardiovasc. Res., 1994, 28, 1815–1820 J. Clin. Invest., 1997, 99, 2059; Science, 1994, 264, 569–571; Cell., 1994, 79, 1157–1164; Proc. Natl. Acad. Sci. USA, 1996, 93, 9764–9769). Tumour cells also use that integrin during their invasive phase, especially in the case of melanomas, and to ensure their survival on contact with the extracellular matrix (Proc. Natl. Acad. Sci. USA, 1992, 89, 1557–1561 and 1994, 91, 8856–8860).

$\alpha_v\beta_5$ integrin, another vitronectin receptor, is also associated with angiogenesis in addition to $\alpha_v\beta_3$ integrin, the two integrins taking part via two distinct routes in the induction of angiogenesis (Science, 1995, 270 1500–1502).

Finally, $\alpha_{IIb}\beta_3$ integrin or GPIIb/IIIa is a fibrinogen receptor, and is responsible for platelet aggregation.

Blocking the interaction of the $\alpha_v\beta_3$ and $\alpha_v\beta_5$ integrins with their ligands is therefore likely to inhibit the adhesion, migration and survival of various cell types, effects that contribute to blocking angiogenesis, inflammation, bone resorption, restenosis, metastases and tumour growth.

The compounds of the invention have a novel structure giving them an antagonistic character towards $\alpha_v\beta_3$ and $\alpha_v\beta_5$ receptors of vitronectin, and rendering them selective in relation to $\alpha_{IIb}\beta_3$ integrins. It will accordingly be possible for them to be useful in the treatment of pathologies characterised by deregulation of the expression or activation of $\alpha_v\beta_3$ and/or $\alpha_v\beta_5$ integrins, while avoiding the side effects in terms of platelet aggregation. In particular, it will be possible for them to be useful in the treatment of cardiovascular disease, inflammation, cancer, osteoporosis, rheumatoid arthritis, psoriasis and retinopathy.

The compounds of the invention will advantageously be useful as inhibitors of tumour growth and metastases formation in the treatment of cancer.

The present invention relates to compounds of formula (I):

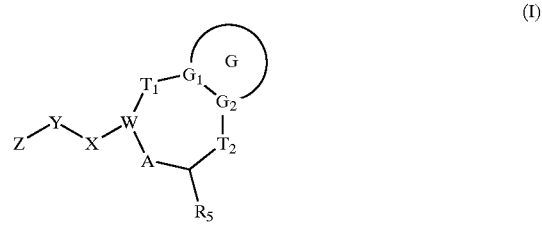

wherein:

G represents a phenyl group or an aromatic or partially unsaturated heterocyclic group having 6 ring members containing 1 or 2 hetero atoms selected from nitrogen and oxygen, unsubstituted or substituted by $R_1$, $R_2$, $R_3$ and/or $R_4$, $G_1$ and $G_2$ independently represent a carbon or nitrogen atom, —$T_1$— represents a group selected from —$CH_2$—$CH_2$—, —CH=CH— and =CH—$CH_2$—, in which case —$T_2$— represents a bond, or —$T_1$— represents a group selected from —$CH_2$— and =CH—, in which case —$T_2$— represents a group —$CH_2$—, =CH—,

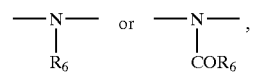

$R_1$, $R_2$, $R_3$ and $R_4$ independently represent a halogen atom or an alkyl, perhaloalkyl, cyano, nitro, $OR_7$, $NR_6R_6'$, $COOR_6$, $CONR_6R_6'$, $COR_6$ or $S(O)_nR_6$ group, n being 0, 1 or 2, $R_5$ represents a —$(CH_2)_m$—$COOR_6$ group, $R_6$ and $R_6'$ independently represent a hydrogen atom or an alkyl, optionally substituted aryl or optionally substituted arylalkyl group, $R_7$ represents a hydrogen atom or an alkyl group, —W— represents a —CH—, =C— or —C= group and —A— represents a —CO—, —$CH_2$—, =CH— or —CH= group, or —W— represents a nitrogen atom and —A— represents a —CO— or —$CH_2$— group, —X— represents a group selected from —CO—$X_1$—, —CO—$NR_6$—$X_1$—, —$NR_6$—CO—$X_1$—, —O—$X_1$—, —$SO_2$—$NR_6$—$X_1$— and —$S(O)_n$—$X_1$—, wherein n is from 0 to 2 and $X_1$ represents an alkylene group, —Y— represents a group selected from —$Y_1$—, —$Y_2$—$Y_1$— and —$Y_1$—$Y_2$—$Y_1$—, wherein $Y_1$ represents an alkylene, alkenylene or alkynylene group and $Y_2$ represents an arylene, heteroarylene, cycloalkylene or heterocycloalkylene group, Z— represents a group selected from $Z_1$—, $Z_{10}$—$NR_6$— and $Z_{10}$—$NR_6$—CO— wherein $Z_{10}$ represents an alkyl group or $Z_1$, and $Z_1$ represents a group selected from $Z_2$—,

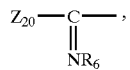

$Z_{20}$—$NR_6$— and $Z_{20}$—$NR_6$—CO— wherein $Z_{20}$ represents an alkyl or heteroalkyl group or $Z_2$, and $Z_2$ represents an optionally substituted heteroaryl group, an optionally substituted heterocycloalkyl group, an optionally substituted heteroarylalkyl group, an optionally substituted heterocycloalkylalkyl group, an optionally substituted fused arylheteroaryl group, an optionally substituted fused arylheterocycloalkyl group, an optionally substituted fused heteroarylheterocycloalkyl group, an optionally substituted fused heterocycloalkylheteroaryl group, an optionally substituted fused heteroarylheteroaryl group or a fused cycloalkylheterocycloalkyl group, m is an integer of from 1 to 6 inclusive, wherein:

the term "alkyl" denotes a linear or branched group having from 1 to 6 carbon atoms, the term "heteroalkyl" denotes an alkyl group in which a carbon atom has been replaced by a hetero atom selected from nitrogen, oxygen and sulphur, the term "alkylene" denotes a linear or branched divalent group having from 1 to 6 carbon atoms, the term "alkenylene" denotes a linear or branched divalent group having from 2 to 6 carbon atoms and from 1 to 3 double bonds, the term "alkynylene" denotes a linear or branched divalent group having from 2 to 6 carbon atoms and from 1 to 3 triple bonds, the term "cycloalkyl" denotes a saturated cyclic group having from 3 to 8 carbon atoms, the term "cycloalkylene" denotes a saturated cyclic divalent group having from 3 to 8 carbon atoms, the term "heterocycloalkyl" denotes a saturated cyclic group having from 5 to 7 ring members and containing from 1 to 3 hetero atoms selected from nitrogen, oxygen and sulphur, the term "aryl" denotes a phenyl group or a naphthyl group, the term "heteroaryl" denotes an unsaturated or partially unsaturated mono- or bicyclic group having from 5 to 11 ring members and containing from 1 to 5 hetero atoms selected from nitrogen, oxygen and sulphur, the expression "fused arylheteroaryl" denotes a polycyclic group formed by an aryl group and a heteroaryl group each as defined hereinabove and conjoined by means of any one of their bonds, the expression "fused arylheterocycloalkyl" denotes a bi- or tri-cyclic group formed by an aryl group and a heterocycloalkyl group each as defined hereinabove and conjoined by means of any one of their bonds, the expression "fused heteroarylheterocycloalkyl" denotes a bi- or tri-cyclic group formed by a heteroaryl group and a heterocycloalkyl group each as defined hereinabove and conjoined by means of any one of their bonds, the expression "fused heterocycloalkylheteroaryl" denotes a bi- or tri-cyclic group formed by a heteroaryl group and a heterocycloalkyl group each as defined hereinabove and conjoined by means of any one of their bonds, the expression "fused heteroarylheteroaryl" denotes a polycyclic group formed by two heteroaryl groups as defined hereinabove and conjoined by means of any one of their bonds, the expression "fused cycloalkylheterocycloalkyl" denotes a bicyclic group formed by a cycloalkyl group and a heterocycloalkyl group each as defined hereinabove and conjoined by means of any one of their bonds, the ending "-ene" denotes that the group in question is a divalent radical having the same meanings as the base radical, the expression "optionally substituted" in connection with the groups heterocycloalkyl, aryl, arylalkyl, heteroaryl, fused arylheteroaryl, fused heteroarylheterocycloalkyl, fused heteroarylheteroaryl and fused arylheterocycloalkyl denotes that those groups are unsubstituted or substituted by one or more halogen atoms or groups alkyl, alkoxy, hydroxy, mercapto, cyano, amino (optionally substituted by one or two alkyl groups), nitro, carboxy, alkoxycarbonyl, aminocarbonyl (optionally substituted by one or two alkyl groups), wherein the heteroaryl and heterocycloalkyl groups may also be substituted by an oxo group, to their enantiomers and diastereoisomers, and also to addition salts thereof with a pharmaceutically acceptable acid or base.

In preferred compounds of the invention, G represents a phenyl group, $G_1$ and $G_2$ each being a carbon atom.

The preferred $R_5$ group of the invention is the group —$CH_2$—$COOR_6$, $R_6$ preferably being an alkyl group or a hydrogen atom.

Preferred compounds of formula (I) are those wherein $T_2$ represents a bond, and even more especially those wherein $T_2$ represents a bond and $T_1$ represents a —CH═CH— group. Another advantageous aspect of the invention concerns compounds of formula (I) wherein $T_2$ represents a group

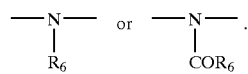

The invention relates especially to compounds of formula (I) wherein A represents a —CO—, —$CH_2$—, ═CH— or —CH═ group (more especially a —$CH_2$— or ═CH— group), and W represents a —CH—, ═C— or —C═ group (more especially a ═C— or —C═ group).

Another advantageous aspect of the invention concerns compounds of formula (I) wherein A represents a —CO— or —$CH_2$— group (more especially a —CO— group) and W represents a nitrogen atom.

In the compounds of formula (I), X will advantageously be selected from —CO—$NR_6$—$X_1$, —$NR_6$—CO—$X_1$ and —O—$X_1$, $R_6$ being more especially a hydrogen atom and $X_1$ preferably representing a methylene group.

In preferred compounds of formula (I), Y represents a $Y_1$ or $Y_1$—$Y_2$—$Y_1$ group wherein $Y_1$ is more especially an alkylene group and $Y_2$ advantageously represents an arylene group. More especially, Y represents a —$(CH_2)_3$— group.

Preferred compounds of the invention are compounds of formula (I) wherein Z represents a heteroaryl, heterocycloalkyl, fused arylheteroaryl or fused heterocycloalkylheteroaryl group or a —$Z_{10}$—$NR_6$ group, $R_6$ being more especially a hydrogen atom and $Z_{10}$ advantageously being selected from the groups heteroaryl, heterocycloalkyl, fused arylheteroaryl and fused heterocycloalkylheteroaryl. The cyclic groups thus preferred for Z advantageously contain one or two nitrogen atoms, such as, for example, the groups pyridine, aminopyridine, (dihydro)pyrrolopyridine, (dihydro)imidazole, 5,6,7,8-tetra-hydro[1,8]naphthyridine or (tetrahydro)pyrimidine.

An especially advantageous aspect of the invention concerns compounds of formula (I) wherein G represents a phenyl group, $G_1$ and $G_2$ each being a carbon atom, $R_5$ represents a —$CH_2$—$COOR_6$ group, $R_6$ being selected from a hydrogen atom and an alkyl group, $T_2$ represents a bond, $T_1$ represents a group selected from —CH=CH— and =CH—$CH_2$—, A represents a —$CH_2$— or =CH— group and W represents a =C— or —C= group. Among those, preference will be given to the compounds wherein X is selected from the groups —CO—$NR_6$—$X_1$—, —$NR_6$—CO—$X_1$— and —O—$X_1$—, $X_1$ being a methylene group, Y represents a group —$Y_1$— or —$Y_1$—$Y_2$—$Y_1$— group in which $Y_1$ is an alkylene group and $Y_2$ represents an arylene group, and Z represents a heteroaryl, heterocycloalkyl, fused arylheteroaryl or fused heterocycloalkylheteroaryl group, or a $Z_{10}$—$NR_6$ group wherein $Z_{10}$ represents a group selected from the groups heteroaryl, heterocycloalkyl, fused arylheteroaryl and fused heterocycloalkylheteroaryl, $R_6$ representing a hydrogen atom.

Another especially advantageous aspect of the invention concerns compounds of formula (I) wherein G represents a phenyl group, $G_1$ and $G_2$ each being a carbon atom, $R_5$ represents a —$CH_2$—$COOR_6$ group, $R_6$ being selected from a hydrogen atom and an alkyl group, $T_2$ represents a bond, $T_1$ represents a —$CH_2$—$CH_2$— group, A represents a —CO— group and W represents a nitrogen atom. Among those, preference will be given to the compounds wherein X is selected from the groups —CO—$NR_6$—$X_1$—, —$NR_6$—CO—$X_1$— and —O—$X_1$—, $X_1$ being a methylene group, Y represents a —$Y_1$— or —$Y_1$—$Y_2$—$Y_1$— in which $Y_1$ is an alkylene group and $Y_2$ represents an arylene group, and Z represents a heteroaryl, heterocycloalkyl, fused arylheteroaryl or fused heterocycloalkylheteroaryl group or a $Z_{10}$—$NR_6$ group wherein $Z_{10}$ represents a group selected from the groups heteroaryl, heterocycloalkyl, fused arylheteroaryl and fused heterocycloalkylheteroaryl, $R_6$ being a hydrogen atom.

Another advantageous aspect of the invention concerns compounds of formula (I) wherein G represents a phenyl group, $G_1$ and $G_2$ each being a carbon atom, $R_5$ represents a —$CH_2$—$COOR_6$ group, $R_6$ being selected from a hydrogen atom and an alkyl group, $T_2$ represents a group

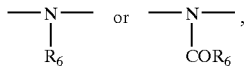

$T_1$ represents a =CH— group, A represents a —$CH_2$— group and W represents a —C= group. Among those, preference will be given to the compounds wherein X is selected from the groups —CO—$NR_6$—$X_1$—, —$NR_6$—CO—$X_1$— and —O—$X_1$—, $X_1$ being a methylene group, —$Y_1$— or —$Y_1$—$Y_2$—$Y_1$— group in which $Y_1$ is an alkylene group and $Y_2$ represents an group, and Z represents a heteroaryl, heterocycloalkyl, fused arylheteroaryl or fused heterocycloalkylheteroaryl group or a $Z_{10}$—$NR_6$ group wherein $Z_{10}$ represents a group selected from the groups heteroaryl, heterocycloalkyl, fused arylheteroaryl and fused heterocycloalkylheteroaryl, $R_6$ representing a hydrogen atom.

The preferred aryl group of the invention is the phenyl group.

Even more especially, the invention relates to the following compounds of formula (I):

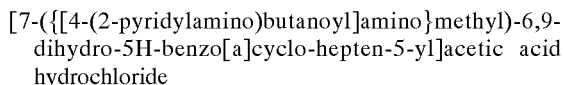

[7-({[4-(2-pyridylamino)butanoyl]amino}methyl)-6,9-dihydro-5H-benzo[a]cyclo-hepten-5-yl]acetic acid hydrochloride

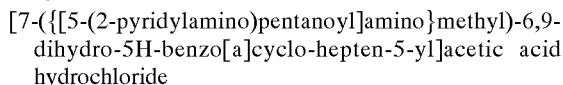

[7-({[5-(2-pyridylamino)pentanoyl]amino}methyl)-6,9-dihydro-5H-benzo[a]cyclo-hepten-5-yl]acetic acid hydrochloride

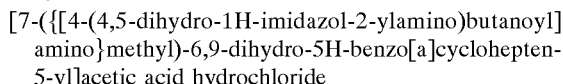

[7-({[4-(4,5-dihydro-1H-imidazol-2-ylamino)butanoyl]amino}methyl)-6,9-dihydro-5H-benzo[a]cyclohepten-5-yl]acetic acid hydrochloride

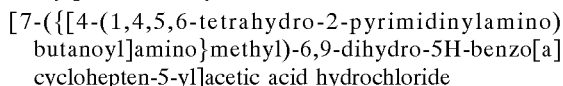

[7-({[4-(1,4,5,6-tetrahydro-2-pyrimidinylamino)butanoyl]amino}methyl)-6,9-dihydro-5H-benzo[a]cyclohepten-5-yl]acetic acid hydrochloride

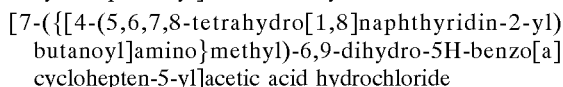

[7-({[4-(5,6,7,8-tetrahydro[1,8]naphthyridin-2-yl)butanoyl]amino}methyl)-6,9-dihydro-5H-benzo[a]cyclohepten-5-yl]acetic acid hydrochloride

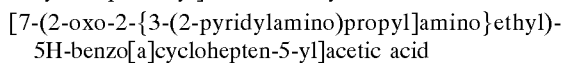

[7-(2-oxo-2-{3-(2-pyridylamino)propyl]amino}ethyl)-5H-benzo[a]cyclohepten-5-yl]acetic acid

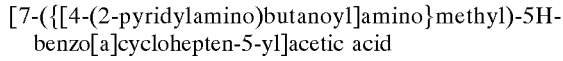

[7-({[4-(2-pyridylamino)butanoyl]amino}methyl)-5H-benzo[a]cyclohepten-5-yl]acetic acid

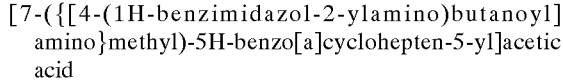

[7-({[4-(1H-benzimidazol-2-ylamino)butanoyl]amino}methyl)-5H-benzo[a]cyclohepten-5-yl]acetic acid

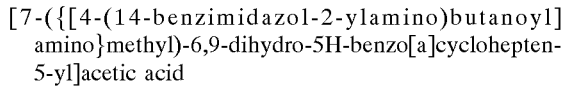

[7-({[4-(14-benzimidazol-2-ylamino)butanoyl]amino}methyl)-6,9-dihydro-5H-benzo[a]cyclohepten-5-yl]acetic acid Amongst the pharmaceutically acceptable acids there may be mentioned hydrochloric, hydrobromic, sulphuric, phosphonic, acetic, trifluoroacetic, lactic, pyruvic, malonic, succinic, glutaric, fumaric, tartaric, maleic, citric, ascorbic, methanesulphonic, camphoric acid etc . . .

Amongst the pharmaceutically acceptable bases there may be mentioned sodium hydroxide, potassium hydroxide, triethylamine, tert-butylamine, etc . . .

The present invention relates also to a process for the preparation of the compounds of formula (I).

The process for the preparation of the compounds of formula (I) is characterised in that:

when, in the compounds of formula (I) it is desired to obtain, A represents a —CO—, —$CH_2$—, =CH— or —CH= group and W represents a —CH—, =C— or —C= group, the starting material used is a compound of formula (II/a):

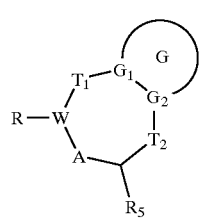

(II/a)

wherein G, $G_1$, $G_2$, $T_1$, $T_2$ and $R_5$ are as defined for formula (I), W and A are as defined hereinabove, and R represents a CHO, CN or AlkOOC—CH= group, which, when R represents a formyl group, is subjected to a Wittig or Homer Emons reaction so as to homologise the chain carrying the aldehyde function, by using the appropriate reagent, to yield a compound of formula (III/a):

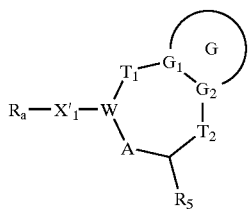

(III/a)

wherein G, $G_1$, $G_2$, $T_1$, $T_2$, $R_5$, A and W are as defined hereinabove, $X'_1$ represents an alkylene or alkenylene group having from two to six carbon atoms and $R_a$ represents a cyano, formyl or alkoxycarbonyl group according to the reagent chosen, which compound (III/a), with the compounds of formula (III/b):

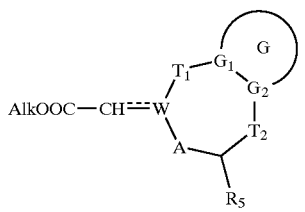

(III/b)

a particular case of the compounds of formula (II/a) wherein G, $G_1$, $G_2$, $T_1$, $T_2$, $R_5$, W and A are as defined hereinabove and Alk represents an alkyl group, the broken lines indicating the optional presence of a double bond, constitute the entirety of the compounds of formula (III-1):

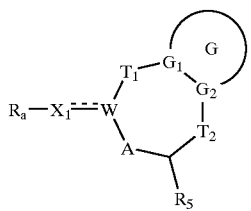

(III-1)

wherein G, $G_1$, $G_2$, $T_1$, $T_2$, W, A and $R_a$ are as defined hereinabove and $X_1$ is as defined for formula (I), or, when, in the compounds of formula (I) it is desired to obtain, A represents a —CO— or —CH$_2$— group and W represents a nitrogen atom, the starting material used is a compound of formula (II/b):

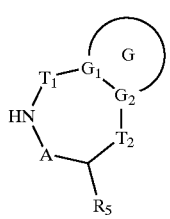

(II/b)

wherein G, $G_1$, $G_2$, $T_1$, $T_2$ and $R_5$ are as defined for formula (I) and A is as defined hereinabove, which is condensed, in basic medium, with a compound of formula $R_b$—$X_1$—Hal, wherein $X_1$ is as defined for formula (I), Hal represents a halogen atom and $R_b$ represents an alkoxycarbonyl or hydroxy group, the latter groups optionally being protected, to yield a compound of formula (III-2):

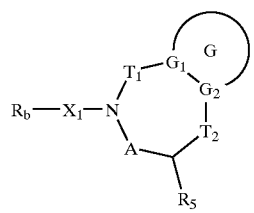

(III-2)

wherein G, $G_1$, $G_2$, $T_1$, $T_2$, $R_5$, $R_b$, A and $X_1$ are as defined hereinabove, the compounds (III-1) and (III-2) constituting the totality of the compounds of formula (III):

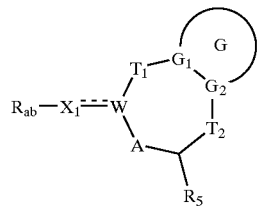

(III)

wherein G, $G_1$, $G_2$, $T_1$, $T_2$, $R_5$, W, A and $X_1$ are as defined for formula (I) and $R_{ab}$ has the same meanings as the groups $R_a$ and $R_b$ combined, the $R_{ab}$ group of which compound (III) is either reduced in alcohol, or deprotected when it represents a masked hydroxy group, to yield a compound of formula (IV):

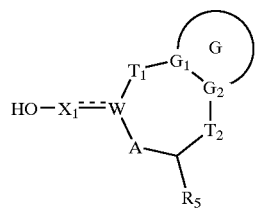

(IV)

wherein G, $G_1$, $G_2$, $T_1$, $T_2$, $R_5$, W, A and $X_1$ are as defined for formula (I), which is subjected to a halogenation reaction to yield a compound of formula (V):

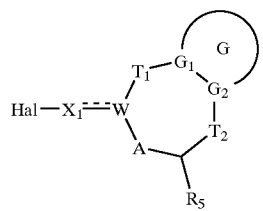

(V)

wherein G, $G_1$, $G_2$, $T_1$, $T_2$, $R_5$, A, W and $X_1$ are as defined hereinabove and Hal represents a halogen atom, which is treated, in basic medium, with a compound of formula Z—Y—OH wherein Z and Y are as defined for formula (I), to yield a compound of formula (I/a):

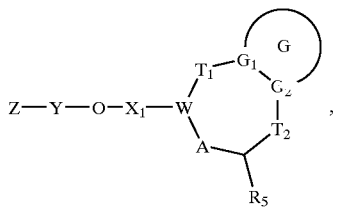

(I/a)

a particular case of the compounds of formula (I) wherein G, $G_1$, $G_2$, $T_1$, $T_2$, $R_5$, $X_1$, W, A, Y and Z are as defined for formula (I), or which is treated, in basic medium, with a compound of formula Z—Y—SH wherein Z and Y are as defined for formula (I), to yield a compound of formula (I/b):

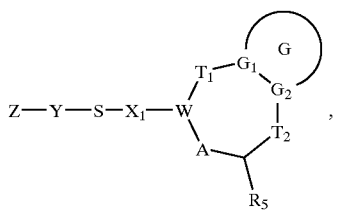

(I/b)

a particular case of the compounds of formula (I) wherein G, $G_1$, $G_2$, $T_1$, $T_2$, $R_5$, $X_1$, W, A, Y and Z are as defined for formula (I), the sulphur atom of which may be oxidised to yield a compound of formula (I/c):

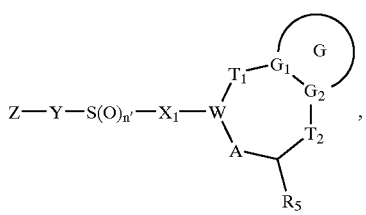

(I/c)

a particular case of the compounds of formula (I) wherein G, $G_1$, $G_2$, $T_1$, $T_2$, $R_5$, $X_1$, W, A, Y and Z are as defined for formula (I) and n' represents an integer 1 or 2, or, which compound of formula (V), subjected to the action of a cyclic imide in basic medium, followed by treatment with hydrazine in alcoholic medium, yields an amine of formula (VI):

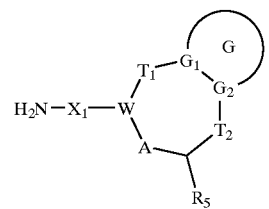

(VI)

wherein G, $G_1$, $G_2$, $T_1$, $T_2$, $R_5$, $X_1$, A and W are as defined hereinabove, it being possible furthermore for the compound of formula (VI) to be obtained directly, when $X_1$ represents a $CH_2$ group, by reduction of a compound of formula (II/a) wherein R represents a CN group, which compound of formula (VI) is treated with a compound of formula (VII):

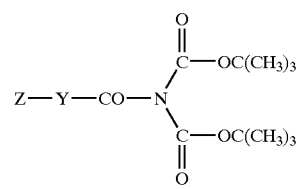

(VII)

wherein Z and Y are as defined for formula (I), to yield a compound of formula (I/d):

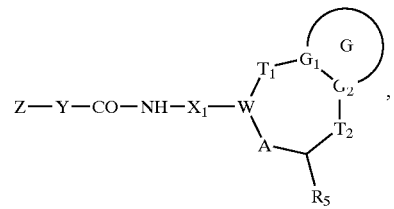

(I/d)

a particular case of the compounds of formula (I) wherein G, $G_1$, $G_2$, $T_1$, $T_2$, $R_5$, $X_1$, A, W, Z and Y are as defined for formula (I), or is treated with a sulphonyl chloride of formula Z—Y—$SO_2$—Cl, wherein Z and Y are as defined for formula (I), to yield a compound of formula (I/e):

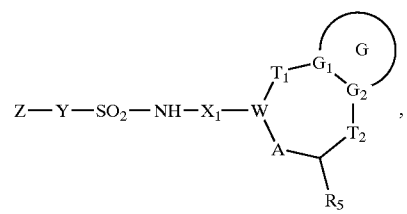

(I/e)

a particular case of the compounds of formula (I) wherein G, $G_1$, $G_2$, $T_1$, $T_2$, $R_5$, $X_1$, A, W, Z and Y are as defined hereinabove for formula (I), or the $R_{ab}$ group of which compound of formula (III) is converted into the corresponding acid to yield a compound of formula (VIII):

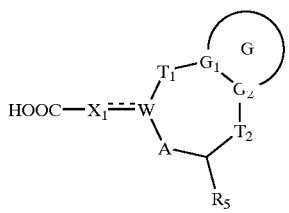
(VIII)

wherein G, $G_1$, $G_2$, $T_1$, $T_2$, $R_5$, W, A and $X_1$ are as defined for formula (I),
which is subjected either to the action of an amine of formula Z—Y—$NH_2$ or the corresponding salt to yield a compound of formula (I/f):

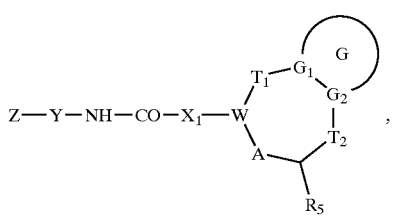
(I/f)

a particular case of the compounds of formula (I) wherein G, $G_1$, $G_2$, $T_1$, $T_2$, $R_5$, A, W, $X_1$, Z and Y are as defined for formula (I),
or to the action of an amine of formula:

to yield a compound of formula (IX):

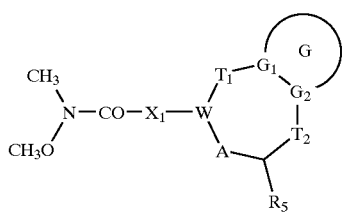
(IX)

wherein G, $G_1$, $G_2$, $T_1$, $T_2$, $R_5$, A, W and $X_1$ are as defined hereinabove,
which is then subjected to the action of a lithium compound of formula Z—Y—Li, wherein Y and Z are as defined for formula (I), to yield a compound of formula (I/g):

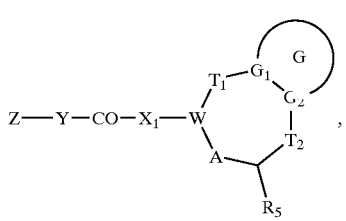
(I/g)

a particular case of the compounds of formula (I) wherein G, $G_1$, $G_2$, $T_1$, $T_2$, $X_1$, W, A, Z and Y are as defined for formula (I), which compounds (I/a) to (I/g), which constitute the totality of the compounds of formula (I), may, if desired, be purified according to a conventional purification technique, are optionally separated into their stereoisomers according to a conventional separation technique, are, if desired, converted into their addition salts with a pharmaceutically acceptable acid or base.

A variant of the process described above when, in the compounds of formula (I) it is desired to obtain, A represents a CO group and W represents a nitrogen atom, comprises using as starting material a compound of formula (II/b) as defined hereinabove, which is condensed in basic medium with a compound of formula Z—Y—X(P), wherein Z, Y and X are as defined for formula (I) and (P) represents a leaving group (for example a halogen atom or a tosyl group), to yield, directly, a compound of formula (I/h):

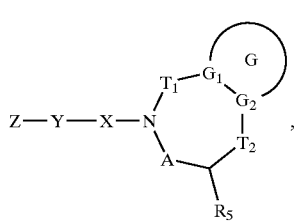
(I/h)

a particular case of the compounds of formula (I) wherein G, $G_1$, $G_2$, $T_1$, $T_2$, $R_5$, X, Y and Z are as defined for formula (I).

Another advantageous variant of the process described hereinabove when, in the compounds of formula (I) it is desired to obtain, Z represents a $Z_{10}NR_6$ group, comprises using as starting material a compound of formula (X):

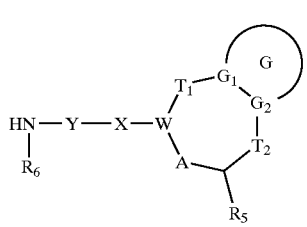
(X)

wherein Y, X, W, $T_1$, G, $G_1$, $G_2$, $T_2$, A, $R_5$ and $R_6$ are as defined for formula (I),
which is condensed, in basic medium or in the presence of a catalyst, with a compound of formula (XI):

(XI)

wherein $Z_{10}$ is as defined for formula (I) and (P') represents a leaving group (for example a halogen atom, a tosyl group or a methylthio or thioxo group)
to yield a compound of formula (I/i), a particular case of the compounds of formula (I):

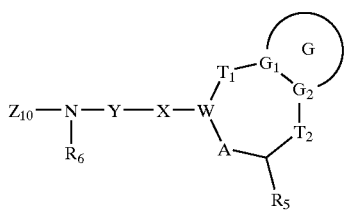

(I/i)

wherein $Z_{10}$ $R_6$ Y, X, W, A, $T_1$, $T_2$, $G_1$, $G_2$, $R_5$ and G are as defined hereinabove, which may, if desired, be purified according to a conventional purification technique, which is optionally separated into its stereoisomers according to a conventional separation technique, which is converted, if desired, into its addition salts with a pharmaceutically acceptable acid or base.

The starting materials used are either known or are prepared according to known procedures.

In particular, the compounds of formula (II/a) wherein G, $G_1$ and $G_2$ together form a phenyl group may be prepared in the following manner, starting from 5,6,8,9-tetrahydro-7H-benzocyclohepten-7-one (2):

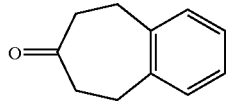

(2)

The compound (2) may be subjected to a dihalogenation reaction in the position α to the carbonyl to yield, after an elimination reaction in basic medium, the unsaturated compound (3):

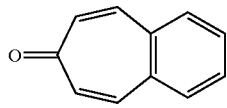

(3)

which is treated in the presence of mercury salts with a ketene acetal of formula (4):

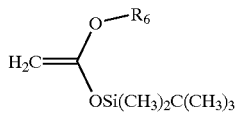

(4)

wherein $R_6$ is as defined for formula (I), to yield a compound of formula (5):

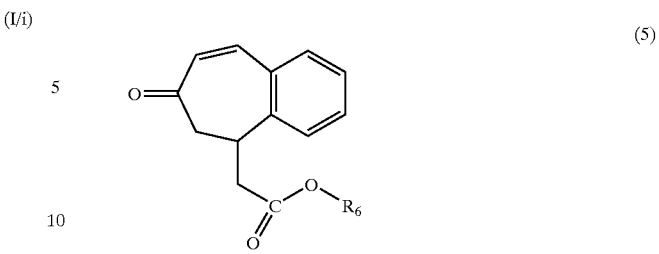

(5)

wherein $R_6$ is as defined hereinabove, which is treated:

either with chloromethyltrimethylsilane in basic medium to yield, after rearrangement in the presence of silica, a compound of formula (6-II/a):

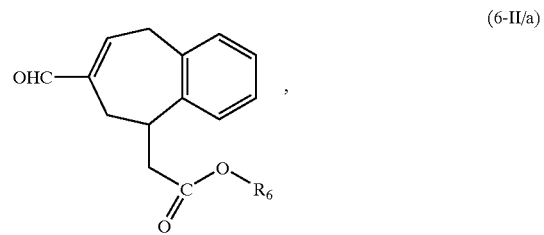

(6-II/a)

a particular case of the compounds of formula (II/a) wherein $R_6$ is as defined for formula (I), or with methyllithium to yield, after dehydration, a compound (7):

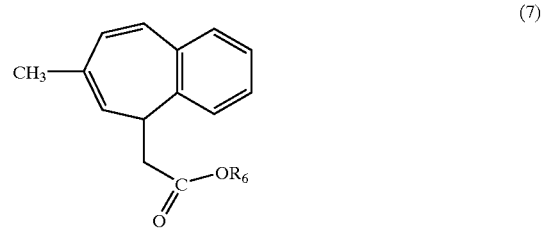

(7)

wherein $R_6$ is as defined hereinabove, the methyl of which is oxidised with an appropriate reagent to yield the corresponding aldehyde (8-II/a):

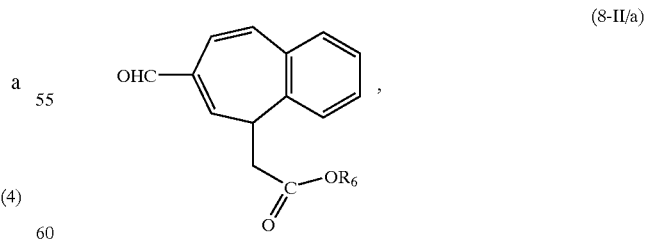

(8-II/a)

a particular case of the compounds of formula (II/a) wherein $R_6$ is as defined for formula (I).

The ketone (2) as defined hereinabove may also be treated with trimethylsilyl chloride in strong basic medium to yield, after oxidation, the unsaturated compound (9):

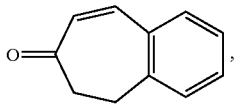
(9)

which is condensed in basic medium with a compound of formula Hal—$(CH_2)_m$—$COOR_6$, wherein m and $R_6$ are as defined for formula (I) and Hal represents a halogen atom, to yield a compound (10):

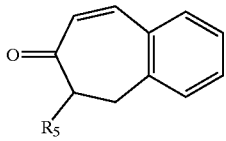
(10)

wherein $R_5$ is as defined for formula (I),
which compound (10) is subjected to the action of carbon monoxide in the presence of a base in a THF/water medium to yield a compound (11-II/a):

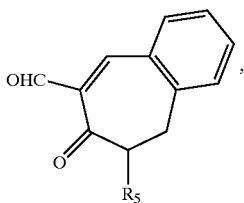
(11-II/a)

a particular case of the compounds of formula (II/a) wherein $R_5$ is as defined for formula (I).

The symmetric ketone (2) can also be converted into the dissymmetric ketone (12):

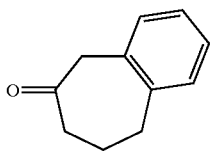
(12)

in accordance with the procedure described in J.O.C., 1980, 45 3028,
which compound (12) may be subjected to a dihalogenation reaction to yield, after an elimination reaction, a compound of formula (13):

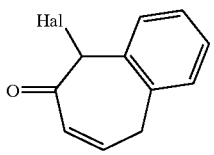
(13)

wherein Hal represents a halogen atom,
which is treated:
either with a ketene acetal of formula (4) as defined hereinabove, in the presence of mercury salts, to yield a compound of formula (14):

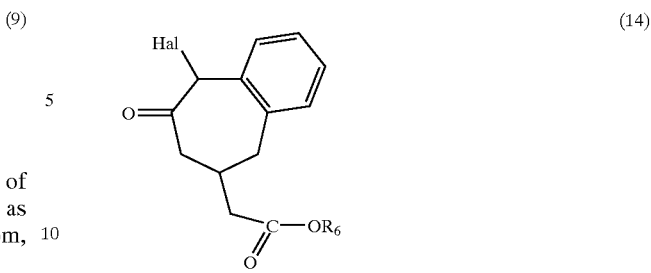
(14)

wherein $R_6$ is as defined for formula (I) and Hal represents a halogen atom,
which is subjected to a Wittig-type reaction using (methoxymethyl)triphenyl-phosphonium chloride to yield, after treatment in acidic medium, a compound of formula (15)

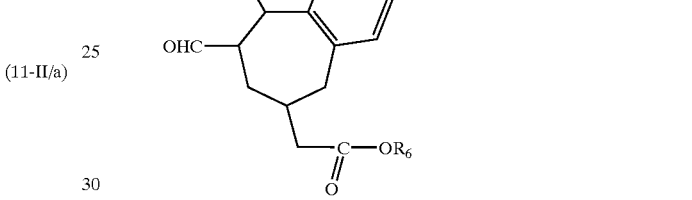
(15)

which, after treatment in basic medium yields an unsaturated aldehyde (16-II/a):

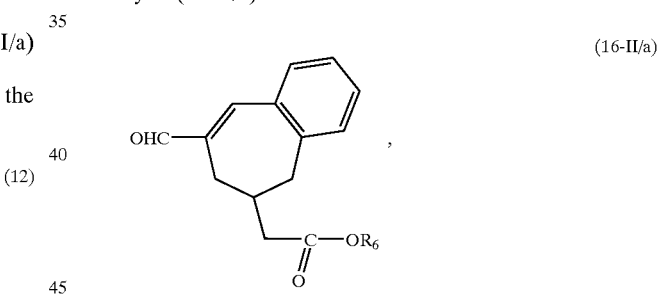
(16-II/a)

a particular case of the compounds of formula (II/a) wherein $R_6$ is as defined for formula (I).
or with a dialkyl malonate in basic medium to yield, after heating, a compound of formula (17):

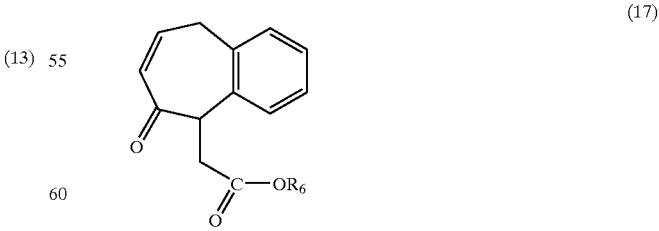
(17)

wherein $R_6$ represents an alkyl group,
which is subjected to the action of carbon monoxide in basic medium in a THF/water medium to yield an aldehyde of formula (18-II/a):

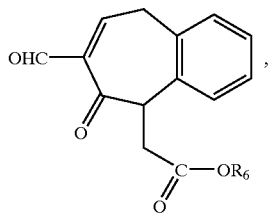
(18-II/a)

a particular case of the compounds of formula (II/a) wherein $R_6$ represents an alkyl group.

The compound (5) as defined hereinabove may be subjected to a Wittig-type reaction using an alkoxymethylene-triphenylphosphorane to yield a compound of formula (19-II/a):

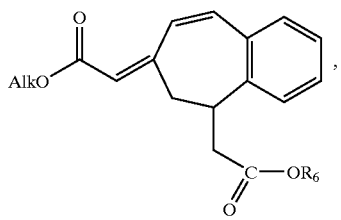
(19-II/a)

a particular case of the compounds of formula (II) wherein $R_6$ is as defined for formula (I) and Alk represents an alkyl group.

The compounds of formula (II/b) wherein G, $G_1$, and $G_2$ together form a phenyl group may be prepared starting from β-tetralone, (20):

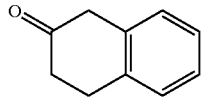
(20)

which is treated in acidic medium with sodium azide to yield the compound (21):

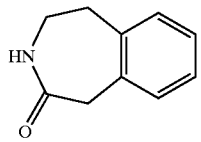
(21)

which, following protection of the nitrogen of the cyclic amide function, is subjected in basic medium to the action of a compound of formula Hal—$(CH_2)_m$—$COOR_6$, wherein m and $R_6$ are as defined for formula (I) and Hal represents a halogen atom, to yield a compound of formula (22-II/b):

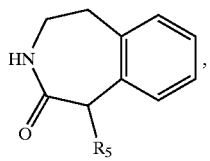
(22-II/b)

a particular case of the compounds of formula (II/b) wherein $R_5$ is as defined for formula (I).

The compounds of formula (II/a) wherein R represents a CN group, $C_1$, $G_2$ and G represent a phenyl group and $T_2$ represents a NH, $NR_6$ or $NCOR_6$ group can be prepared starting from a compound of formula (23):

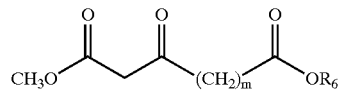
(23)

wherein m and $R_6$ are as defined for formula (I), which is condensed in succession with (2-aminophenyl)methanol and the anhydride of formula $R'_6$ $COOCOR'_6$ (wherein $R'_6$ is as defined for formula (I)) and then subjected to the action of a halogenation agent, such as $PBr_3$ for example, to yield a compound of formula (24):

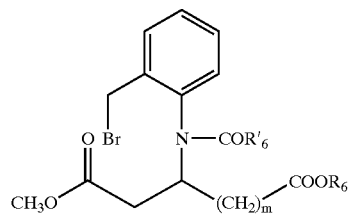
(24)

wherein m, $R_6$ and $R'_6$ are defined hereinabove, which is converted into the corresponding acid chloride and is then cyclised in the presence of a palladium catalyst to obtain a compound of formula (25):

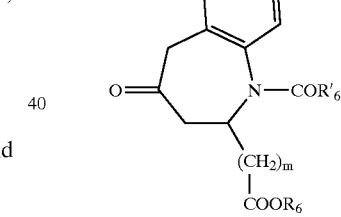
(25)

wherein m, $R_6$ and $R'_6$ are as defined hereinabove, which is reacted, after conversion into the corresponding enol ether, with LiCN in the presence of $Pd(PPh_3)_4$ to yield a compound of formula (26):

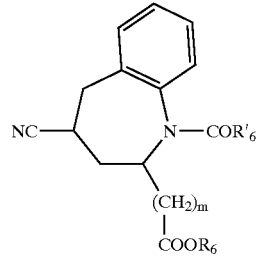
(26)

wherein m, $R_6$ and $R'_6$ are as defined hereinabove, which may be sujected to the action of a reducing agent, such as $NaBH_4$ for example, to obtain a compound of formula (27):

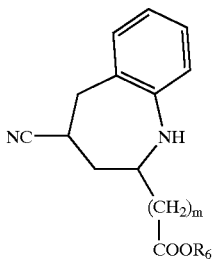

(27)

wherein m and $R_6$ are as defined hereinabove, which is condensed with a compound of formula (P″)-R′$_6$, wherein P″ represents a leaving group and R′$_6$ is as defined hereinabove, to yield a compound of formula (28):

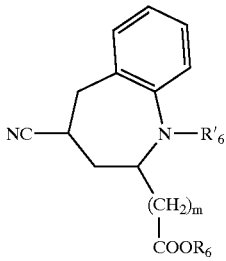

(28)

wherein m, $R_6$ and R′$_6$ are as defined hereinabove,

The present invention relates also to pharmaceutical compositions comprising as active ingredient at least one compound of formula (I), alone or in combination with one or more pharmaceutically acceptable inert, non-toxic excipients or carriers.

Amongst the pharmaceutical compositions according to the invention there may be mentioned more especially those which are suitable for oral, parenteral, nasal or transdermal administration, tablets or dragées, sublingual tablets, gelatin capsules, lozenges, suppositories, creams, ointments, dermal gels, etc.

The useful dosage varies according to the age and weight of the patient, the nature and the severity of the disorder and also the administration route, which may be oral, nasal, rectal or parental. Generally, the unit dose ranges from 0.05 to 500 mg for a treatment of from 1 to 3 administrations per 24 hours.

The Examples which follow illustrate the invention and do not limit it in any way. The structures of the compounds described have been confirmed by customary spectroscopic techniques.

Preparation 1 tert-Butyl (7-formyl-6,9-dihydro-5H-benzocyclohepten-5-yl)-acetate

Step a: 6,8-Dibromo-5,6,8,9-tetrahydro-7H-benzocyclohepten-7-one

A solution of bromine (17.19 ml; 333.7 mmol) in 300 ml of 1,2-dichloroethane is added dropwise to a solution of 5,6,8,9-tetrahydro-7H-benzocyclohepten-7-one in 500 ml of 1,2-dichloroethane at ambient temperature. After the addition, the reaction mixture is heated at reflux for 3 hours. After returning to ambient temperature, the mixture is concentrated to yield the expected compound.

Step b: Benzocyclohepten-7-one

The compound obtained in the above Step (166.8 mmol) is dissolved in 1 litre of dimethylformamide. Lithium bromide (86.93 g; 1 mol) and lithium carbonate (73.96 g; 1 mol) are then added to the reaction mixture, and the mixture is heated at reflux for one night. After concentration, the residue is taken up in dichloromethane and washed with water. The organic phases are collected, dried over magnesium sulphate and concentrated. The residue obtained is purified by chromatography on silica gel (eluant toluene/ethyl acetate 95/5) to yield the expected product.

Step c: tert-Butyl (7-oxo-6,7-dihydro-5H-benzocyclohepten-5-yl)acetate

Mercury iodide (10.32 g; 22.27 mmol) is added at −78° C., with stirring, to a solution of the compound described in the above Step (14.19 g; 90.9 mmol) in 120 ml of dichloromethane. After stirring for 5 minutes (1-tert-butoxyvinyloxy)tert-butyl-dimethylsilane (0.38 mol per mmol of compound) is added dropwise over a period of approximately 20 minutes. Stirring is maintained for 2 hours at −78° C. After hydrolysis using 150 ml of an aqueous ammonium chloride solution and extraction with dichloromethane, the organic phase is dried over magnesium sulphate and concentrated. The residue obtained is purified by chromatography of silica gel (petroleum ether/ethyl acetate 95/5) to yield the expected compound.

Step d: tert-Butyl (7-formyl-6,9-dihydro-5H-benzocyclohepten-5-yl)acetate 100 ml of a solution of sec-butyllithium in cyclohexane (1.3M) and tetramethylethylenediamine (14.41 g; 124 mmol; 18.8 ml) are added dropwise in succession at −78° C., with stirring and under an anhydrous atmosphere, to a solution of chloromethyltrimethylsilane (14.6 g; 119 mmol; 16.6 ml) in 180 ml of tetrahydrofuran. After stirring for one hour at −78° C., a solution of the compound described in the above Step (15.4 g; 56 mmol) in 30 ml of tetrahydrofuran is added dropwise. After 1 hour 30 minutes cold, the temperature if allowed to return to ambient temperature over a period of 1 hour 30 minutes. The mixture is then hydrolysed using 800 ml of a saturated aqueous ammonium chloride solution and extracted with diethyl ether. After drying over magnesium sulphate and concentrating the organic phase, the residue obtained is taken up in 250 ml of dichloromethane and stirred in the presence of 60 g of silica gel. After filtration, the filtrate is concentrated to yield the title product.

Preparation 2

Ethyl [5-(2-tert-butoxy-2-oxoethyl)-5,6-dihydro-7H-benzocyclohepten-7-ylidene]acetate The compound described in Step C of Preparation 1 (8.45 g; 31 mmol) is heated at reflux in tetrahydrofuran in the presence of carbethoxymethylenetriphenylphosphorane (21.7 g; 62 mmol), under an inert atmosphere, for 10 days. The reaction mixture is concentrated and the residue obtained is taken up in a minimum amount of dichloromethane and then pentane is added. The resulting precipitate is filtered off and the filtrate is concentrated and then purified by chromatography on silica gel (eluant dichloromethane/petroleum ether 1/1) to yield the expected compound in the form of a mixture of cis and trans isomers.

Preparation 3

Methyl [1-(2-tert-butoxy-2-oxoethyl)-2-oxoethyl)-2-oxo-1,2,4,5-tetrahydro-3H-3-benzazepin-3-yl]acetate Step a: 1,3,4,5-Tetrahydro-2H-3-benzazepin-2-one While maintaining the temperature of the reaction mixture below 65° C., $NaN_3$ (13.35 g; 205.2 mmol) is added in small portions to a solution, heated beforehand to 55° C., of β-tetralone (25 g; 171 mmol) in a mixture of 150 ml of glacial acetic acid and concentrated sulphuric acid (33.39 g; 342 mmol; 18.25 ml). Stirring is then carried out for 8 hours at 70° C. After returning to ambient temperature, the reaction mixture is poured onto ice and diluted with ethyl acetate. After extracting the organic phase, drying over magnesium sulphate and concentrating, the residue obtained is purified by chromatography on silica gel (eluant ethyl acetate) to yield the expected compound.

Step b: 3-(Trimethylsilyl)-1,3,4,5-tetrahydro-2H-3-benzazepin-2-one

The compound described in the above Step (2 g; 12.4 mmol) is suspended in 30 ml of anhydrous pentane at ambient temperature under an inert atmosphere. Triethylamine (2.5 g; 24.8 mmol; 3.45 ml) and then chlorotrimethylsilane (2.69 g; 24.8 mmol; 3.15 ml) are added thereto. After stirring for 4 hours at ambient temperature, the reaction mixture is filtered under an inert atmosphere, and the filtrate is concentrated under an inert atmosphere to yield the expected product.

Step c: tert-Butyl (2-oxo-2,3,4,5-tetrahydro-1H-3-benzazepin-1-yl)acetate

Lithium diisopropylamide is produced in conventional manner (20 minutes at 0° C.) from diisopropylamine (18.6 mmol; 2.6 ml) and n-butyllithium (1.6M in hexane) (18.6 mmol; 11.6 mol) in 30 ml of tetrahydrofuran and the reaction mixture is then cooled to –78° C. The compound described in the above Step, diluted with 30 ml of tetrahydrofuran, is added dropwise. The anion is formed in 15 minutes at –20° C., and then the reaction mixture is cooled again to –78° C. After stirring for 5 minutes, tert-butyl bromoacetate (2.4 g; 12.4 mmol; 2 ml) is added dropwise. After stirring for 30 minutes, the reaction mixture is hydrolysed with a saturated aqueous sodium chloride solution and extracted with diethyl ether. After filtration, concentration and purification by chromatography on silica gel, the expected product is obtained.

Step d: Methyl [1-(2-tert-butoxy-2-oxoethyl)-2-oxo-1,2,4,5-tetrahydro-3H-3-benzazepin-3-yl]acetate A 60% strength dispersion of sodium hydride (22 mg; 0.55 mmol) in oil is added to a solution, cooled to 0° C., of the compound described in the above Step (100 mg; 0.416 mmol) in 6 ml of anhydrous tetrahydrofuran and 300 µl of dimethylformamide. After stirring for 30 minutes, tetrabutylammonium iodide (16 mg; 0.04 mmol) and methyl bromomethylacetate (69 mg; 0.455 mmol; 43 µl) are added in succession. Stirring is carried out for 1 hour at 0° C. and then the reaction mixture is hydrolysed with a saturated aqueous ammonium chloride solution. After extraction with diethyl ether, the organic phase is dried over magnesium sulphate and concentrated to yield the title product.

Preparation 4 tert-Butyl (7-formyl-5H-benzocyclohepten-5-yl) acetate

Step a: tert-Butyl (7-hydroxy-7-methyl-6,7-dihydro-5H-benzocyclohepten-5-yl)acetate A 1M solution of methyllithium (100 ml, 100 mmol) in tetrahydrofuran is added dropwise at –78° C. to a solution of the compound described in Step c of Preparation 1 (22.7 g; 83.32 mmol) in 225 mol of tetrahydrofuran. The reaction is maintained with stirring at –78° C. for 3 hours. The reaction mixture is hydrolysed with 160 ml of a saturated aqueous ammonium chloride solution and extracted with diethyl ether. The organic phase is dried over magnesium sulphate, concentrated and purified by chromatography on silica gel (eluant petroleum ether/ethyl acetate 80/20) to yield the expected product.

Step b: tert-Butyl (7-methyl-5H-benzocyclohepten-5-yl) acetate

Triethylamine (18.74 g; 185.2 mmol) and thionyl chloride (11.01 g; 92.6 mmol) are added in succession to a solution, cooled to 0° C., of the compound described in the above Step (26.7 g; 92.6 mmol) in 165 ml of dichloromethane. Stirring is carried out at 0° C. for 10 minutes. The reaction mixture is poured onto ice and extracted with dichloromethane. The organic phase is dried over magnesium sulphate and concentrated to yield the expected product.

Step c: tert-Butyl (7-formyl-5H-benzocyclohepten-5-yl) acetate

The compound obtained in the above Step (23.7 g; 90.25 mmol) is dissolved in a 250/4 dioxane/water mixture at ambient temperature. Selenium dioxide (28.4 g; 256 mmol) is then added and the reaction mixture is heated at reflux for 1 hour. After cooling and filtration over Celite, the filtrate is concentrated and purified by chromatography on silica gel (eluant: petroleum ether/dichloromethane 50/50) to yield the title product.

Preparation 5 tert-Butyl (7-{[(4-aminobutanoyl)amino]methyl}-6,9-dihydro-5H-benzo[a]cyclohepten-5-yl)acetate Step a: tert-Butyl (7-{[(4-bromobutanoyl)amino]methyl}-6,9-dihydro-5H-benzo[a]cyclohepten-5-yl)acetate Under an argon atmosphere at 0° C. and with stirring $Et_3N$ (1.4 g; 13.9 mmol; 1.93 ml) and 4-bromobutanoyl chloride (2.5 g; 13.9 mmol; 1.61 ml) are added dropwise in succession to a solution of the compound obtained in Step b of Example 23 (4 g; 13.9 mmol) dissolved in 45 ml of $CH_2Cl_2$. The reaction mixture is stirred for 45 minutes at 0° C. and then hydrolysed. After extraction with dichloromethane, drying and concentration, the title product is obtained in the form of a viscous yellow oil, which is used as it is for the subsequent reaction.

Step b: tert-Butyl-(7-{[(4-azidobutanoyl)amino]methyl}-6,9-dihydro-5H-benzo[a]cyclohepten-5-yl)acetate Sodium azide (1.8 g; 27.8 mol) is added in one portion at ambient temperature, with stirring and under an argon atmosphere, to a solution of the compound obtained in Step a in 190 ml of DMF. The reaction mixture is then heated at 80° C. for 6 hours and subsequently allowed to rest for the night at ambient temperature. After concentration a brown oil corresponding to the title product is obtained, which is used as it is for the subsequent reaction.

Step c: tert-Butyl (7-{[(4-aminobutanoyl)amino]methyl}-6,9-dihydro-5H-benzo[a]cyclohepten-5-yl)acetate Triphenylphosphine (5.47 g; 20.85 mmol) is added in one portion at ambient temperature, with stirring, to a solution of the compound obtained in Step b (13.9 mmol) in 50 ml of THF. After stirring for 3 hours, $H_2O$ is added to the reaction mixture (3.3 ml) and stirring is carried out for 10 hours at ambient temperature. After concentration and purification on silica gel of the residue obtained (eluant: $CH_2Cl_2$/EtOH/$NH_4OH$ 95/5/0.5), the title product is obtained in the form of a yellow oil.

Preparation 6

Methyl [4-(aminomethyl)-2,3-dihydro-1H-1-benzazepin-2-yl]acetate

Step a: Dimethyl 3-[2-(hydroxymethyl)anilino]pentanedioate

There are added in succession, to a solution of dimethyl 3-oxopentanedioate (5 g; 28.71 mmol; 4.2 ml) in dichloroethane (125 ml) at 0° C., (2-aminophenyl)methanol (2.95 g; 23.93 mol), and then NaBH(OAc)$_3$ (6 g; 28.71 mol) in small portions.

The reaction mixture is then stirred for 12 hours at ambient temperature and subsequently concentrated to dryness. The residue is then chromatographed on silica (eluant: heptane/EtOAc) to yield the title product.

Step b: Dimethyl 3-[2-(bromomethyl)(trifluoroacetyl)anilino]pentanedioate

A solution of the compound obtained in Step a (3.15 g; 11.22 mmol), of Et$_3$N (16.73 g; 16.53 mol; 23 ml) and of Et$_2$O (41 ml) is cooled to 0° C. A solution of trifluoroacetic anhydride (2.7 g; 13 mol; 1.8 ml) in 2 ml of Et$_2$O is added dropwise thereto and the reaction mixture is stirred for one hour at 0° C.

The reaction mixture is then washed with a H$_2$SO$_4$ solution (0.1 N) and subsequently with H$_2$O. After drying and concentrating under reduced pressure, the compound obtained is redissolved in a CH$_2$Cl$_2$ (15.5 ml)/Et$_2$O (21.5 ml) mixture, and then PBr$_3$ (9 g; 3.36 mol) is added at 0° C. The reaction mixture is subsequently stirred for a few minutes at ambient temperature and then for 30 minutes at reflux and then poured into an Et$_2$O/ice mixture. The Et$_2$O phase is extracted and washed with a saturated aqueous NaCl solution. After concentration and drying, a residue is obtained which is chromatographed on silica gel (eluant:heptane/Et$_2$O) to obtain the title product.

Step c: Methyl 3-[2-bromomethyl)(trifluoroacetyl)anilino]-5-chloro-5-oxopentanoate The compound obtained in Step b (3.34 g; 76 mmol) is diluted with 5.5 ml of a 1/1 dioxane/water mixture. Lithium hydroxide (0.319 g; 7.6 mmol) is added, and the reaction is stirred at ambient temperature for a few hours. The reaction mixture is then extracted once with diethyl ether. The aqueous phase is subsequently acidified with HCl (0.1N) and extracted with dichloromethane. The organic phase is concentrated and the residue obtained is diluted with 10 ml of toluene and treated with SOCl$_2$ (0.97 g; 8.16 mol, 0.595 ml). The reaction mixture is stirred at 70° C. for 2 hours and then concentrated to dryness and evaporated 3 times with cyclohexane. The residue obtained, corresponding to the title project, is used as it is in the subsequent reaction.

Step d: Methyl [4-oxo-1-(trifluoroacetyl)-2,3,4,5-tetrahydro-1H-1-benzazepin-2-yl]acetate A solution of the compound obtained in Step c (2.72 g; 6.12 mmol), in 50 ml of 1,2-dimethoxyethane, is added under an argon atmosphere to a suspension of Pd(PPh$_3$)$_2$Cl$_2$ (0.25 g; 0.306 mmol)(5 mol %) and zinc powder (0.8 g; 12.24 mmol), and stirred in 50 ml of DME at ambient temperature. After stirring for one hour, the reaction mixture is filtered over Celite, concentrated and chromatographed on silica gel to yield the title product.

Step e: Methyl (1-(trifluoroacetyl)-4-{[(trifluoromethyl)sulphonyl]oxy}-2,3-dihydro-1H-1-benzazepin-2-yl)acetate EtMgBr (4.66 ml), (1.0 N in Et$_2$O) is added to a solution of diisopropylamine (0.602 g; 4.6 mmol; 811 µl) in Et$_2$O (50 ml) at 0° C., and the reaction mixture is stirred at ambient temperature for 12 hours. After cooling the reaction mixture to 0° C., 10.34 mmol of HMPA are added, followed by the compound obtained in Step d (1.16 g, 4.89 mmol). The reaction mixture is then stirred for 6 hours at ambient temperature, and subsequently N-phenyltriflimide (1.66 g; 4.66 mmol) is added in one portion. The reaction mixture is then stirred for 15 hours at ambient temperature and subsequently at reflux for 6 hours. After cooling, the reaction mixture is washed with HCl (10% aq.), (2×80 ml) then H$_2$O (2×80 ml), NaOH (10% aq.) (2×80 ml) and finally NaCl (2×80 ml). After drying, concentration and purification on silica gel (eluant: heptane/EtOAc), the title compound is obtained.

Step f: Methyl [4-cyano-1-(trifluoroacetyl)-2,3-dihydro-1H-1-benzazepin-2-yl]acetate A solution of the compound obtained in Step e (1.35 g; 293 mmol) in 16 ml of anhydrous toluene is added to a mixture of LiCN (0.5 M in DMF) (11.72 ml; 5.86 mmol), (Ph$_3$P)$_4$Pd (237 mg; 0.205 mmol) and 12-crown-4 (36 mg; 0.205 mmol) under an argon. atmosphere. The reaction mixture is stirred at ambient temperature for 6 hours. Water (10 ml) is added to the reaction mixture, and the organic phase is extracted with diethyl ether. After drying and concentration, the residue obtained is purified on silica gel (eluant:heptane/EtOAc) to yield the title product.

Step g: Methyl [4-(aminomethyl)-2,3-dihydro-1H-1-benzazepin-2-yl]acetate nBu$_4$NBH$_4$ is added at ambient temperature to a solution of the compound obtained in Step f (0.792 g; 2.34 mmol) in dichloroethane (10 ml). The reaction mixture is then heated at 45° C. for 8 hours. 10 ml of HCl (10%) are subsequently added and heating is carried out for 1 hour at 50° C. After concentration, the residue is chromatographed on silica (CH$_2$Cl$_2$/EtOH/NH$_4$OH) to yield the title compound.

Preparation A

2-[(3-Aminopropyl)amino]pyridine dihydrochloride

Step a: N-tert-Butoxycarbonyl-1,3-propanediamine

A solution of BOC$_2$O (21.825 g; 0.1 mol 23 ml) in 100 ml of dichloromethane is added dropwise at 0° C., with stirring, to a solution of 1,3-propanediamine (78.13 g; 1 mol; 85 ml) in 500 ml of dichloromethane. The reaction mixture is then stirred for 30 minutes at ambient temperature and subsequently concentrated. The residue obtained is taken up in water and filtered and the filtrate is extracted twice with 200 ml of dichloromethane each time. The organic phases are dried over magnesium sulphate and concentrated to yield the expected product.

Step b: 2{[3-(tert-Butoxycarbonylamino)propyl]amino}prydine N-oxide

The compound obtained in the above Step (9.4 g; 53.9 mmol) is taken up in 52 ml of tert-amyl alcohol and stirred in the presence of sodium hydrogen carbonate (22.64 g; 269.5 mmol). 2-Chloropyridine N-oxide (10.75 g; 64.72 mmol) is then slowly added to the reaction mixture and the mixture is heated at reflux for 48 hours. After cooling, the reaction mixture is diluted with 100 ml of dichloromethane and subsequently filtered. The filtrate is concentrated and purified by chromatography on silica gel (eluant dichloromethane/ethanol/ammonium hydroxide, 90/10/1) to yield the expected product.

Step c: 2-{[(3-tert-Butoxycarbonylamino)propyl]amino}pyridine

10% palladium on carbon (4.0 g), and also (32.44 g; 394 mmol, 40 ml) of cyclohexene, are added under argon to solution of the compound obtained in the above step (9 g; 34 mmol) in 400 ml of ethanol. The mixture is heated at reflux for 8 hours. The reaction mixture is then cooled, filtered, concentrated and purified by chromatography on silica gel (eluant dichloromethane/ethanol, 95/5) to yield the expected product.

Step d: 2-[(3-Aminopropyl)amino]pyridine dihydrochloride

The compound described in Step (7.4 g; 27.7 mmol) is dissolved in 275 ml of dichloromethane and the solution is stirred at 0° C. Gaseous HCl is bubbled through the solution for 30 min, and the reaction mixture is then stirred at ambient temperature for one hour. The mixture is subsequently diluted with 2 liters of diethyl ether and the precipitate formed is filtered off and dried to yield the title product.

Preparation B

2[(4-Aminobutyl)amino]pyridine dihydrochloride

The expected product is obtained in accordance with the procedure described in Preparation A, with the replacement of 1,3-propanediamine with 1,4-butanediamine.

Preparation C

2-[(2-Aminoethyl)amino]pyridine dihydrochloride

The expected product is obtained in accordance with the procedure described in Preparation A, with the replacement of 1,3-propanediamine with 1,2-ethylenediamine.

Preparation D

2-[(3-Aminomethyl)benzylamino]pyridine dihydrochloride

The expected product is obtained in accordance with the procedure described in Preparation A, with the replacement of 1,3-propanediamine with meta-xylenediamine.

Preparation E

Di(tert-butyl) 3-[(tert-butoxycarbonyl)(2-pyridyl)amino]prop-anoylimidocarbonate Step a: 3-(2-Pyridylamino)propionic acid N-oxide A solution of β-alanine hydrochloride (27 g; 300 mmol) in 250 ml of water is stirred in the presence of sodium hydrogen carbonate (65 g; 770 mmol) at ambient temperature. 2-chloropyridine N-oxide (25 g, 151 mol) is then added and the reaction mixture is heated at reflux for 72 hours. After cooling, the reaction mixture is washed with dichloromethane. The aqueous phase is acidified with concentrated hydrochloric acid. The precipitate formed is filtered off, and the filtrate is concentrated and then purified by chromatography on silica gel (eluant dichloromethane/ethanol/ammonium hydroxide, 90/8/2) to yield the expected product.

Step b: 3-(2-Pyridylamino)propionic acid

The compound described in the above Step (2.1 g; 11.53 mmol) is diluted with a mixture of dioxane (40ml) and water (10 ml) and stirred in the presence of cyclohexene (17.25 g; 210 mmol; 14 ml) and 10% palladium on carbon (2 g). The reaction mixture is heated at reflux for 3 hours. After cooling, the mixture is filtered, and the filtrate is concentrated to yield the expected product.

Step c: 3-(2-Pyridylamino)propionamide

The compound described in the above Step (3.9 g; 23.32 mmol) is diluted with 400 ml of methanol and acetyl chloride (3.66 g; 46.6 mmol; 3.3 ml) is added dropwise. The mixture is heated at reflux for 2 hours. The reaction mixture is concentrated and the residue is taken up in a saturated solution of ammoniacal methanol in a Parr apparatus, which is heated at 130° C. for 72 hours. The mixture is cooled and concentrated to yield the expected product.

Step d: tert-Butyl 3-amino-3-oxopropyl(2-pyridyl)carbamate

The compound obtained in the above Step (2.6 g; 15.74 mmol) is stirred at ambient temperature under argon in 15 ml of tert-butanol. Di(tert-butyl) dicarbonate (6.87 g; 31.48 mol; 6.6 ml) is added dropwise and the reaction mixture is stirred for 48 hours. The mixture is concentrated and the residue obtained is purified by chromatography on silica gel (eluant dichloromethane/ethanol, 95/5) to yield the expected product.

Step e: Di(tert-butyl) 3-[(tert-butoxycarbonyl)(2-pyridyl)amino]propanoyl-imidodicarbonate Di(tert-butyl) dicarbonate (862 mg; 395 mmol; 0.910 ml) and dimethylaminopyridine (23 mg; 0.188 mmol) are added in succession, at ambient temperature, to a solution of the compound obtained in the above Step (500 mg; 1.88 mmol) in 5 ml of acetonitrile stirred under argon. The reaction mixture is stirred for 16 hours at ambient temperature and then concentrated. The residue obtained is purified by chromatography on silica gel (eluant dichloromethane/ethyl acetate, 30/1) to yield the expected product.

Preparation F

Di(tert-butyl) 4-[(tert-butoxycarbonyl)(2-pyridyl)amino]butanoyl-imidodicarbonate The expected product is obtained in accordance with the procedure described in Preparation E, with the replacement of β-alanine hydrochloride with 4-aminobutyric acid.

Preparation G

Di(tert-butyl) 5-[(tert-butoxycarbonyl)(2-pyridyl)amino]-pentanoylimidodicarbonate The expected product is obtained in accordance with the procedure described in Preparation E, with the replacement of β-alanine hydrochloride with 5-aminovaleric acid.

Preparation H

Di(tert-butyl) 3-[(2-pyridylamino)methyl]benzoylimidocarbonate

Step a: 3-[(2-Pyridylamino)methyl]benzonitrile

Sodium triacetoxyborohydride (23 g; 108 mmol) is added in small portions to a solution, stirred under an argon atmosphere, of 3-cyanobenzaldehyde (10 g; 63.7 mmol) and 2-aminopyridine (6 g; 63.7 mmol) in 300 ml of 1,2-dichloroethane. After stirring for 12 hours at ambient temperature, the reaction mixture is hydrolysed with methanol and concentrated. The residue obtained is purified by chromotography on silica gel (eluant petroleum ether/ethyl acetate, 3/1 then 2/1 and 1/1) to yield the expected product.

Step b: 3-[(2-Pyridylamino)methyl]benzamide

The compound obtained in the above Step (2 g; 9.56 mmol) is diluted with 6.6 ml of water. Trimethylsilane chloride (34.3 g; 315.5 mmol; 40 ml) is added dropwise thereto. The reaction mixture is stirred for 7 days at ambient temperature and then concentrated. The residue is taken up in ethyl acetate and washed with a saturated aqueous sodium hydrogen carbonate solution. The organic phases are dried over magnesium sulphate and concentrated to yield the expected product.

Step c: Di(tert-butyl) 3-[(2-pryidylamino)methyl]benzoylimidocarbonate

The expected product is obtained in accordance with the procedure described in Step e of Preparation E, using as starting material the compound described in the above Step.

Preparation I

2-[(5-Hydroxy-1-pentyl)amino]pyridine

The expected product is obtained in accordance with the procedure described in Steps b and c of Preparation A, using as starting material 5-amino-1-pentanol.

Preparation J

2-[(4-Hydroxy-1-butyl)amino]pyridine

The expected product is obtained in accordance with the procedure described in Steps b and c of Preparation A, using as starting material 4-amino-1-butanol.

Preparation K

2-[(3-Hydroxy-1-propyl)amino]pyridine

The expected product is obtained in accordance with the procedure described in Steps b and c of Preparation A, using as starting material 3-amino-1-propanol.

Preparation L

{3-[(2-Pyridylamino)methyl]phenyl}methanol

Step a: [3-({[tert-Butyl(dimethyl)silyl]oxy}methyl)phenyl] methanol

A solution of 1,3-benzenedimethanol (2 g; 14.47 mmol) in 50 ml of dimethylformamide is stirred at ambient temperature. Imidazole (1.97 g; 28.94 mmol) and tert-butyl (dimethyl)silane chloride (2.18 g; 14.47 mmol) are added in succession. After stirring for 12 hours, the reaction mixture is diluted with ether and washed with a saturated aqueous sodium chloride solution. After extraction, the ethereal phase is dried over magnesium sulphate and concentrated to yield the expected compound.

Step b: 3-({[tert-Butyl(dimethyl)silyl]oxy}methyl) benzaldehyde

A solution of the compound described in the above Step (1.73 g; 6.85 mmol) in 20 ml of dichloromethane is stirred in the presence of activated manganese dioxide (6 g; 69 mmol). After stirring for 24 hours at ambient temperature, the reaction mixture is filtered over Celite, and the filtrate is concentrated to yield the expected product.

Step c: N-[3-({[tert-Butyl(dimethyl)silyl]oxy}methyl) benzyl]-2-pyridinamine

A solution of the compound described in the above Step (1.3 g; 5.23 mmol) in 21 ml of 1,2-dichloroethane is stirred at ambient temperature. 2-Aminopyridine (492 mg; 5.23 mmol) and then sodium triacetoxyborohydride (1.88 g; 8.89 mmol) are added in succession. After stirring for 12 hours at ambient temperature, the reaction mixture is concentrated and the residue is purified by chromatography on silica gel (eluant: petroleum ether/ethyl acetate 4/1) to yield the expected product.

Step d: {3-[(2-Pyridylamino)methyl]phenyl}methanol

A solution of the compound described in the above Step (1.8 g; 5.49 mmol) in 27 ml of anhydrous tetrahydrofuran is stirred at 0° C. Tetrabutylammonium fluoride (1M in tetrahydrofuran, 3.3 ml; 3.29 mmol) is added to the reaction mixture and stirring is carried out from 0° C. to ambient temperature over 10 hours. The reaction mixture is then diluted with ether and washed with a saturated aqueous sodium chloride solution. After extraction, the ethereal phase is dried over magnesium sulphate, concentrated and purified by chromatography on silica gel (eluant: petroleum ether/ethyl acetate 1/1) to yield the expected product.

Preparation M

N1-(4,5,6,7-Tetrahydro-3H-azepin-2-yl)-1,3-propanediamine

Step a: tert-Butyl 2-(4,5,6,7-tetrahydro-3H-azepin-2-yl) ethylcarbamate

A solution of N-tert-butoxycarbonyl-1,3-propanediamine (2 g; 11.48 mmol), described in Step a of Preparation A, in 1 ml of ethanol is added to a solution of 2-methoxy-4,5,6, 7-tetrahydro-3H-azepine (1.46 g; 11.48 mmol; 1.7 ml) in 4 ml of absolute ethanol. After stirring for 8 hours at ambient temperature, the reaction mixture is concentrated to yield the expected product.

Step b: N1-(4,5,6,7-Tetrahydro-3H-azepin-2-yl)-1,3-propanediamine

The expected product is obtained in accordance with the procedure described in Step d of Preparation A, starting from the compound described in the above Step.

Preparation N

N1-(4,5-Dihydro-1H-imidazo-2-yl)-1,3-propanediamine

Step a: tert-Butyl 3-(4,5-dihydro-1H-imidazo-2-ylamino) propylcarbamate 2-methylthioimidazoline hydroiodide (25 g; 102 mmol) and then diisopropylamine (13.18 g; 102 mmol; 18 ml) are added at ambient temperature, under an argon atmosphere, to a stirred solution of N-tert-butoxycarbonyl-1,3-propanediamine (8.9 g; 51 mmol) in 150 ml of dimethyl acetamide. The reaction mixture is heated at 100° C. for 12 hours. After cooling and concentration, the residue obtained is purified by chromatography on silica gel (eluant ethyl acetate/petroleum ether 4/1)to yield the desired product.

Step b: N1-(4,5-Dihydro-1H-imidazo-2-yl)-1,3-propanediamine

The expected product is obtained in accordance with the procedure described in Step d of Preparation A, starting from the compound described in the above Step.

Preparation O

N-[3-(Aminomethyl)benzyl]-4,5-dihydro-1H-imidazol-2-amine

Step a: tert-Butyl 3-(aminomethyl)benzylcarbamate

The expected product is obtained in accordance with the procedure described in Step a of Preparation A, using as starting material meta-xylenediamine.

Step b: tert-Butyl 3-[(4,5-dihydro-1H-imidazol-2-ylamino) methyl]benzylcarbamate The expected product is obtained in accordance with the procedure described in Step a of Preparation N, using as starting material the compound described in the above Step.

Step c: N-[3-(Aminomethyl)benzyl]-4,5-dihydro-1H-imidazol-2-amine

The expected product is obtained in accordance with the procedure described in Step d of Preparation A, using as starting material the compound described in the above Step.

Preparation P

N-(4,5,6,7-Tetrahydro-3H-azepin-2-yl)aminobutyric acid

The expected product is obtained in accordance with the procedure described in Step a of Preparation M, with the replacement of N-tert-butoxycarbonyl-1,3-propanediamine with γ-aminobutyric acid.

Preparation Q tert-Butyl 2-[{4-[bis(tert-butoxycarbonyl)amino]-4-oxobutyl}-(tert-butoxycarbonyl)amino]-1H-benzimidazole-1-carboxylate

Step a: tert-Butyl 2-[(tert-butoxycarbonyl)amino]-1H-benzimidazole-1-carboxylate $BOC_2O$ (34.8 g; 160 mmol) is added at ambient temperature, with stirring, to a solution of aminobenzimidazole (10.66 g; 80 mmol) in 200 ml of tert-butanol. Stirring is maintained for 10 hours. The precipitate is filtered off and rinsed with pentane to yield the expected product.

Step b: tert-Butyl 2-[(4-amino-4-oxybutyl)(tert-butoxycarbonyl)amino]-1H-benzimidazole-1-carboxylate The compound obtained in the above Step (6 g; 18 mmol) is dissolved in 60 ml of dimethylformamide. γ-Hydroxybutyramide (930 mg; 9 mmol) is added to the solution, and the reaction mixture is cooled to 0° C. Triphenylphosphine (4.18 g; 13.5 mmol) and then DEAD (2.35 g; 13.5 mmol) are added. The reaction is stirred for 15 hours, from 0° C. to ambient temperature. After concentration, the residue obtained is purified by chromatography on silica gel (eluant dichloromethane/ethanol 40/1) to yield the expected product.

Step c: tert-Butyl 2-[{4-[bis(tert-butoxycarbonyl)amino]-4-oxybutyl}(tert-butoxycarbonyl)amino]-1H-benzimidazole-1-carboxylate The expected product is obtained in accordance with the procedure described in Preparation E, Step e, starting from the compound described in the above Step.

Preparation R

4-[(4,5-Dihydro-1H-imidazol-2-yl)amino]butyric acid

The expected product is obtained in accordance with the procedure described in Preparation N, with the replacement of N-tert-butoxycarbonyl-1,3-propanediamine with tert-butyl 4-aminobutanoate, followed by hydrolysis in accordance with the procedure described in Step d of Preparation A.

Preparation S

3-(1,4,5,6-Tetrahydro-2-pyrimidinylamino)benzoic acid

Step a: 3-{[Imino(methylsulphanyl)methyl]amino}benzoic acid

Methyl iodide (18 g; 127.4 mmol; 7.93 ml) is added at ambient temperature, under an argon atmosphere, to a solution of 3-[(aminocarbothioyl)amino]benzoic acid (25 g; 127.4 mmol) in 375 ml of anhydrous tetrahydrofuran, and then the reaction mixture is heated at 75° C. for 2 hours. After cooling and concentration, the residue is taken up in ether and the precipitate formed is filtered off to yield the expected product.

Step b: 3-(1,4,5,6-Tetrahydro-2-pyrimidinylamino)benzoic acid

Triethylamine (3.03 g; 30 mmol; 4.17 ml), 4-dimethylaminopyridine (420 mg; 3.4 mmol) and 1,3-diaminopropane (2.22 g; 30 mmol) are added to solution of the compound obtained in the above Step (10.1 g; 30 mmol) in 15 ml of anhydrous dimethylformamide, and the reaction mixture is heated at 145° C. for 5 hours. After cooling to ambient temperature, the reaction mixture is taken up in water. The precipitate formed is filtered off, redissolved in water, and then acidified with 36% hydrochloric acid. The mixture is concentrated to yield the expected product.

Preparation T

N-(4,5,6,7-Tetrahydro-3H-azepin-2-yl)aminopentanoic acid

The expected product is obtained in accordance with the procedure described in Step a of Preparation M, with the replacement of N-tert-butoxycarbonyl-1,3-propanediamine with 5-aminopentanoic acid.

Preparation U tert-Butyl 2-[{5-[bis(tert-butoxycarbonyl)amino]-5-oxopentyl}-(tert-butoxycarbonyl)amino]-1H-benzimidazole-1-carboxylate

The expected product is obtained in accordance with the procedure described in Preparation Q, with the replacement of γ-hydroxybutyramide with δ-hydroxypentanamide in Step b.

Preparation V

5-[(4,5-Dihydro-1H-imidazol-2-yl)amino]pentanoic acid

The expected product is obtained in accordance with the procedure described in Preparation N, with the replacement of N-tert-butoxycarbonyl-1,3-propanediamine with tert-butyl 5-aminopentanoate, followed by hydrolysis in accordance with the procedure described in Step d of Preparation A.

Preparation W tert-Butyl 2-(methylthio)-5,6-dihydro-1(4H)-pyrimidinecarboxylate

Triethylamine (3.92 g; 38.7 mmol; 5.54 ml) and then $BOC_2O$ (9.3 g; 42.57 mmol) are added at ambient temperature, with stirring, to a solution of 2-methylthio-2-tetrahydropyrimidine iodidrate (10 g; 38.7 mmol) in 38 ml of dichloromethane. Stirring is maintained for 10 hours. The reaction mixture is then evaporated to dryness and subsequently taken up in pentane. The evaporated filtrate yields the title product in the form of a colourless oil.

Preparation X tert-Butyl 2-(methylthio)-4,5-dihydro-1H-imidazole-1-carboxylate

The procedure is as in Preparation W, with the replacement of 2-methylthio-2-tetrahydropyrimidine iodidrate with 2-methylthio-2-imidazoline iodidrate.

Preparation Y

Di(tert-butyl) 5-methoxy-2-thioxo-1H-benzimidazole-1,3(2H)-dicarboxylate

NaH (60% in oil) (5.55 g; 138 mmol) is added in small portions at 10° C., with stirring, to a solution of 2-mercapto-5-methoxybenzimidazole (10 g; 55.5 mmol) in solution in 400 ml of tetrahydrofuran under argon. The reaction mixture is then stirred for 30 minutes at 0° C., and then $BOC_2O$ (26.64 g; 122 mmol) is added in one go. Stirring of the reaction mixture is then carried out for 18 hours at ambient temperature. The reaction mixture is diluted with methanol, filtered over Celite and then concentrated to dryness. The residue obtained is subsequently taken up in a 1/1 mixture of petroleum ether/isopropyl ether. The solid which precipitates is then suction-filtered off to yield the title product in the form of a white powder.

Preparation Z

Di(tert-butyl) 3-[(tert-butoxycarbonyl)(2-pyridylmethyl)amino]-propanoylimidodicarbonate step a: 3-[(2-Pyridylmethyl)amino]propanamide Acrylamide (3.29 g; 46.24 mmol) and triethylamine (0.468 g; 4.624 mmol; 6.62 µl)) are added dropwise in succession at ambient temperature, with stirring and under an argon atmosphere, to a solution of 2-(aminomethyl)-pyridine (5 g; 46.24 mmol; 4.77 ml) in 19 ml of dimethylformamide. The reaction mixture is then heated to 40° C. and stirred at that temperature for 72 hours. At the end of the reaction, the reaction mixture is concentrated and the residue is purified by chromatography on silica gel (eluant: $CH_2Cl_2$/EtOH/$NH_4OH$ 80/20/2) to yield the title product in the form of a yellow oil.

Step b: tert-Butyl 3-amino-3-oxopropyl(2-pyridylmethyl)carbamate $BOC_2O$ (18.5 g; 84.8 mmol) is added in one portion to the compound obtained in Step a (7.6 g; 42.4 mmol) stirred at ambient temperature in 50 ml of tert-butanol. After stirring for 72 hours at ambient temperature, the reaction mixture is concentrated and the residue obtained is purified by chromatography on silica gel (eluant: $CH_2Cl_2$/EtOH 95/5) to yield the title product.

Step c: Di(tert-butyl) 3-[(tert-butoxycarbonyl)(2-pyridylmethyl)amino]-propanoylimidodicarbonate The procedure is as in Step e of Preparation E, starting from the compound obtained in Step b.

Preparation $A_1$ tert-Butyl 2-{[{3-[bis(tert-butoxycarbonyl)amino]-3-oxopropyl}-(tert-butoxycarbonyl)amino]methyl}-1H-benzimidazole-1-carboxylate The procedure is as in Preparation Z, with the replacement of 2-(aminomethyl)pyridine with 2-(aminomethyl)benzimidazole.

Preparation $A_2$ 4-(5,6,7,8-Tetrahydro[1,8]naphthyridin-2-yl)butanoic acid

Step a: Ethyl 4-[1,8]naphthyridin-2-ylbutanoate

A solution consisting of 2-aminonicotinaldehyde (0.7 g; 5.8 mmol), ethyl 5-oxohexanoate (1.83 g; 11.6 mmol; 1.85 ml), L-proline (0.166 g; 1.45 mmol) and 50 ml of EtOH is heated at 90° C., with stirring, for 6 hours. The reaction mixture is then concentrated and the residue is purified by chromatography on silica gel (eluant: EtOAc) to yield the title product in the form of a beige solid.

Step b: Ethyl 4-(5,6,7,8-tetrahydro[1,8]naphthyridin-2-yl)butanoate

The compound obtained in Step a (0.57 g; 2.33 mmol) is dissolved in15 ml of AcOEt and subjected to stirring, in a hydrogen atmosphere, in the presence of 57 mg of Pd/C (10%) for 18 hours. The reaction mixture is then filtered over Celite and concentrated to dryness to yield the title product in the form of a yellow oil.

Step c 4-(5,6,7,8-Tetrahydro[1,8]naphthyridin-2-yl)butanoic acid

The ester obtained in Step b (0.36 g; 1.45 mmol) is dissolved in 10 ml of 6N HCl. The reaction mixture is heated at 55° C. for 4 hours. The reaction mixture is then concentrated, and the residue is taken up in AcOEt. The resulting precipitate, corresponding to the title product, is suction-filtered off over a frit and isolated in the form of a pale yellow solid.

Preparation $A_3$

4-Oxo-4-(2-pyridylamino)butanoic acid

The compound 2-aminopyridine (5 g; 53.02 mmol) is dissolved in 80 ml of THF and heated at 80° C. for 15 hours in the presence of succinic anhydride (5.3 g; 53.08 mmol) and a catalytic amount of $Et_3N$ (0.7 ml). A white solid is observed with precipitates in the reaction mixture and is suction-filtered off, corresponding to the title product.

Preparation $A_4$

Di(tert-butyl) 4-1,3-thiazol-2-ylamino)butanoylimidodicarbonate

The procedure is as in Preparation Q, with the replacement of aminobenzimidazole with 1,3-thiazol-2-ylamine.

EXAMPLE 1 tert-Butyl [7-({[5-(2-pyridylamino)pentyl]oxy}methyl)-6,9-dihydro-5H-benzo[a]cyclohepten-5-yl]acetate Step a: tert-Butyl (7-hydroxymethyl-6,9-dihydro-5H-benzo[a]cyclohepten-5-yl)acetate Sodium borohydride (1.1 g; 28.84 mol) is added in small portions at 0° C., with stirring, to a solution of the compound described in Preparation 1 (8.26 g; 28.84 mmol) in 1.6 liters of a 1/1 methanol/dichloromethane mixture. After stirring for 30 minutes at 0° C., the reaction mixture is concentrated, taken up in dichloromethane and washed with a saturated aqueous sodium chloride solution. The organic phase is dried over magnesium sulphate and concentrated to yield the desired product Step b: tert-Butyl (7-bromomethyl-6,9-dihydro-5H-benzo[a]cyclohepten-5-yl)acetate Carbon tetrabromide (9.05 g; 27.3 mmol), and then triphenylphosphine (7.16 g; 27.3 mmol) dissolved in 35 ml of dichloroethane, are added to a solution, stirred at 0° C., of the compound described in the above Step (7.5 g; 26 mmol) in 30 ml of dichloroethane. The reaction mixture is stirred at 0° C. for 30 minutes and then concentrated. The residue obtained is purified by chromatography on silica gel (eluant petroleum ether/dichloromethane, 1/1) to yield the expected compound.

Step c: tert-Butyl [7-({[5-(2-pyridylamino)pentyl]oxy}methyl)-6,9-dihydro-5H-benzo [a]cyclohepten-5-yl]acetate The compound described in Preparation I (484 mg; 2.68 mmol) dissolved in 4 ml of acetonitrile, and then caesium carbonate (873 mg; 2.68 mmol), are added to a solution, stirred at ambient temperature, of the compound described in the above Step (940 mg; 2.68 mmol) in 4 ml of acetonitrile. The reaction mixture is then heated at 40° C. for 12 hours. Insoluble material is removed by filtration and the filtrate is concentrated and then purified by chromatography on silica gel (eluant petroleum ether/diethyl ether 1/1) to yield the expected product.

EXAMPLE 2

[7-({[5-(2-Pyridylamino)pentyl]oxy}methyl)-6,9-dihydro-5H-benzo[a]cyclohepten-5-yl]acetic acid hydrochloride The compound described in Example 1 (315 mg; 0.65 mmol) is diluted with 8 ml of dichloromethane and stirred at ambient temperature. 16 ml of an ethereal HCl solution (4 N) are then added. The reaction mixture is stirred until the starting material has completely disappeared, which is verified by thin layer chromatography (eluant dichloromethane/ ethanol 95/5). At the end of the reaction, 50 ml of petroleum ether are added to the reaction mixture and the mixture is stirred for several hours. The supernatant is removed and washing the gum with pentane is repeated 3 times. The gum is then taken up in water and washed with dichloromethane. The aqueous phase is subsequently lyophilised and the powder obtained is purified by chromatography on silica gel (eluant dichloromethane/ethanol/acetic acid, 98/2/0.7) to yield the title product.

Elemental microanalysis: $C_{24}H_{30}N_2O_9.HCl$

|  | C | H | N |
|---|---|---|---|
| % Calculated: | 66.88 | 7.25 | 6.50 |
| % Found: | 66.77 | 7.22 | 7.15 |

EXAMPLE 3 tert-Butyl [7-({[4-(2-pyridylamino)butyl] oxy}methyl)-6,9-dihydro-5H-benzo[a]cyclohepten-5-yl]acetate The expected product is obtained in accordance with the procedure described in Example 1 with the replacement, in Step c, of the product described in Preparation I with the product described in Preparation J.

EXAMPLE 4

[7-({[4-(2-Pyridylamino)butyl]oxy}methyl)-6,9-dihydro-5H-benzo[a]cyclohepten-5-yl]acetic acid hydrochloride The expected product is obtained in accordance with the procedure described in Example 2, using as starting material the compound described in Example 3.

Elemental microanalysis: $C_{23}H_{28}N_2O_3.HCl$ (0.8 mol)

|  | C | H | N |
|---|---|---|---|
| % Calculated: | 67.43 | 7.09 | 6.84 |
| % Found: | 67.53 | 6.92 | 6.88 |

EXAMPLE 5 tert-Butyl [7-({[3-(2-pyridylamino)propyl] oxy}methyl)-6,9-dihydro-5H-benzo[a]cyclohepten-5-yl]acetate The expected product is obtained in accordance with the procedure described in Example 1 with the replacement, in Step c, of the product described in Preparation I with the product described in Preparation K.

EXAMPLE 6

[7-({[3-(2-Pyridylamino)propyl]oxy}methyl)-6,9-dihydro-5H-benzo[a]cyclohepten-5-yl]acetic acid hydrochloride The expected product is obtained in accordance with the procedure described in Example 2, using as starting material the compound described in Example 5.

Elemental microanalysis: $C_{22}H_{26}N_2O_3.HCl$ (1.3 mol)

|  | C | H | N |
|---|---|---|---|
| % Calculated: | 63.84 | 6.65 | 6.77 |
| % Found: | 63.81 | 6.66 | 6.78 |

EXAMPLE 7

{7-[({3-[(2-Pyridylamino)methyl]benzyl}oxy) methyl]-6,9-dihydro-5H-benzo[a]cyclohepten-5-yl}acetic acid hydrochloride The expected product is obtained in accordance with the procedure described in Examples 1 and 2 with the replacement, in Step c of Example 1, of the product described in Preparation I with the product described in Preparation L.

Elemental microanalysis: $C_{27}H_{28}N_2O_3.HCl$ (1.2 mol)

|  | C | H | N | Cl |
|---|---|---|---|---|
| % Calculated: | 68.66 | 6.23 | 5.93 | 9.0 |
| % Found: | 68.51 | 6.04 | 6.11 | 7.73 |
| Mass spectrum (ESI in infusin): M + $H^{1+}$ = 429 | | | | |

EXAMPLE 8

[7-(2-Oxo-2-{[3-(2-pyridylamino)propyl] amino}ethyl)-5H-benzo[a]cyclohepten-5-yl]acetic acid trifluoroacetate Step a: [5-(2tert-butoxy-2-oxoethyl)-5,6-dihydro-7H-benzo [a]cyclohepten-5-ylidene]acetic acid The compound described in Preparation 2 (3 g; 8.76 mmol) is stirred vigorously in 6.4 ml of a 1/1 dioxane/water mixture. Lithium hydroxide (0.368 g; 8.76 mmol) is added, and the reaction mixture is stirred at 40° C. for 24 hours. After cooling, the reaction mixture is extracted once with diethyl ether. The aqueous phase is treated with a saturated aqueous ammonium chloride solution and extracted with dichloromethane. The organic phases are combined and concentrated to yield the expected compound.

Step b: tert-Butyl [7-(2-oxo-2-{[3-(2-pyridylamino)propyl] amino}ethyl)-5H-benzo[a]cyclohepten-5-yl]acetate To a solution of the compound described in the above Step (1 g; 3.82 mmol) in 25 ml of anhydrous dimethylformamide there are added in succession the product described in Preparation A (0.856 g; 3.82 mmol), hydroxybenzotriazole monohydrate (0.516 g; 3.82 mmol), diisopropylamine (2.06 g; 15.9 mmol; 2.77 ml) and finally N-ethyl-N'-3-dimethylaminopropylcarbodiimide hydrochloride (0.732 g; 3.82 mmol) at ambient temperature, and the reaction mixture is stirred for 24 hours. After concentration, the residue is taken up in dichloromethane and washed with a saturated aqueous sodium hydrogen carbonate solution. The organic phase is dried over magnesium sulphate, concentrated and purified by chromatography on silica gel (eluant dichloromethane/ethanol 40/1) to yield the expected product.

Step c: [7-(2-Oxo-2-{[3-(2-pyridylamino)propyl]amino}ethyl)-5H-benzo[a]cyclohepten-5-yl]acetic acid trifluoroacetate The compound described in the above Step (190 mg; 0.43 mmol) is stirred in 8 ml of dichloromethane at ambient temperature. Trifluoroacetic acid (979 mg; 8.59 mmol; 660 µl) is added dropwise and stirring is maintained for 24 hours. The reaction mixture is diluted with a mixture of diethyl ether and pentane. The precipitate formed is filtered off and washed with pentane to yield the title product.

Elemental microanalysis: $C_{23}H_{25}N_3O_3.C_2HF_3O_2$ (1.3 mol)

|  | C | H | N |
|---|---|---|---|
| % Calculated: | 56.97 | 4.91 | 7.79 |
| % Found: | 56.82 | 4.87 | 7.60 |

EXAMPLE 9

[7-(2-Oxo-2-{[4-(2-pyridylamino)butyl]amino}ethyl)-5H-benzo[a]cyclohepten-5-yl]acetic acid trifluoroacetate The expected product is obtained in accordance with the procedure described in Example 8 with the replacement, in Step b, of the compound of Preparation A with the compound described in Preparation B.

Elemental microanalysis: $C_{24}H_{27}N_3O_3.C_2HF_3O_2$ (1.3 mol)

|  | C | H | N |
|---|---|---|---|
| % Calculated: | 57.7 | 5.15 | 7.59 |
| % Found: | 57.36 | 4.99 | 7.57 |

EXAMPLE 10

[7-(2-Oxo-2-{[2-(2-pyridylamino)ethyl]amino}ethyl)-5H-benzo[a]cyclohepten-5-yl]acetic acid trifluoroacetate The expected product is obtained in accordance with the procedure described in Example 8 with the replacement, in Step b, of the compound of Preparation A with the compound described in Preparation C.

Elemental microanalysis: $C_{22}H_{23}N_3O_3.C_2HF_3O_2$ (1.1 mol)

|  | C | H | N |
|---|---|---|---|
| % Calculated: | 57.80 | 4.84 | 8.36 |
| % Found: | 57.41 | 4.89 | 8.25 |

EXAMPLE 11

{7-[2-Oxo-2-({3-[(2-pyridylamino)methyl]benzyl}amino)ethyl]-6,9-dihydro-5H-benzo[a]cyclohepten-5-yl}acetic acid trifluoroacetate The expected product is obtained in accordance with the procedure described in Example 8 with the replacement, in Step b, of the compound of Preparation A with the compound described in Preparation D.

Elemental microanalysis: $C_{28}H_{27}N_3O_3.C_2HF_3O_2$

|  | C | H | N |
|---|---|---|---|
| % Calculated: | 59.61 | 4.61 | 6.73 |
| % Found: | 59.75 | 5.12 | 6.29 |

EXAMPLE 12

[7-(2-Oxo-2-{[3-(N1-4,5,6,7-tetrahydro-3H-azepin-2-yl)propyl]-amino}ethyl)-5H-benzo[a]cyclohepten-5-yl]acetic acid trifluoroacetate The expected product is obtained in accordance with the procedure described in Example 8 with the replacement, in Step b, of the compound of Preparation A with the compound described in Preparation M.

EXAMPLE 13

[7-(2-Oxo-2-{[3-(4,5-dihydro-1H-imidazo-2-yl)propyl]-amino}-ethyl)-5H-benzo[a]cyclohepten-5-yl]acetic acid trifluoroacetate The expected product is obtained in accordance with the procedure described in Example 8 with the replacement, in Step b, of the compound of Preparation A with the compound described in Preparation N.

EXAMPLE 14

{7-[2-Oxo-2-({3-[(4,5-dihydro-1H-imidazo-2-ylamino)methyl]benzyl}-amino)ethyl]-6,9-dihydro-5H-benzo[a]cyclohepten-5-yl}acetic acid trifluoroacetate The expected product is obtained in accordance with the procedure described in Example 8 with the replacement, in Step b, of the compound of Preparation A with the compound described in Preparation O.

EXAMPLE 15

[7-({[4-(2-Pyridylamino)butanoyl]amino}methyl)-5H-benzo[a]cyclohepten-5-yl]acetic acid hydrochloride Step a: tert-Butyl [7-(hydroxymethyl)-5H-benzo[a]cyclohepten-5-yl]acetate The expected product is obtained in accordance with the procedure described in Example 1, Step a, with the replacement of the compound described in Preparation 1 with the product described in Preparation 4.

Step b: tert-Butyl {7-[(1,3-dioxo-1,3-dihydro-2H-isoindol-2-yl)methyl]-5H-benzo[a]cylcohepten-5-yl}acetate Phthalimide (1.67 g; 11.3 mmol), triphenylphosphine (2.98 g; 11.3 mmol) and DEAD (1.97 g; 11.3 mmol) are added in succession to a solution, cooled to 0° C., of the compound described in the above Step (2.5 g; 8.7 mmol) in 12 ml of dichloromethane. Stirring is carried out from 0° C. to ambient temperature over 5 hours. After concentration, the residue is purified by chromatography on silica gel (eluant: dichloromethane) to yield the desired product.

Step c: tert-Butyl (7-aminomethyl-5H-benzo[a]cyclohepten-5-yl)acetate

The compound described in the above Step (5.72 g; 13.8 mmol) is diluted with 60 ml of dichloromethane. Hydrazine monohydrate (2.07 g; 41.3 mmol) dissolved in 60 ml of methanol is then added. The reaction mixture is stirred for 24 hours at ambient temperature. The reaction if filtered and the filtrate is concentrated. The residue is taken up in ether and washed with an aqueous 5% sodium carbonate solution. The organic phase is dried over magnesium sulphate, concentrated and purified by chromatography on silica gel (eluant: dichloromethane/ethanol/ammonium hydroxide, 95/5/0.5) to yield the expected product.

Step d: tert-Butyl {7-[({4-[(tert-butoxycarbonyl)(2-pyridyl) amino]butanoyl}-amino)methyl]-5H-benzo[a]cyclohepten-5-yl}acetate A solution of the compound described in Preparation F (1.26 g; 2.63 mmol) in 5 ml of dichloromethane is added dropwise to a solution of the compound described in the above Step (500 mg; 1.76 mmol) in 10 ml of dichloromethane. The reaction mixture is stirred for 24 hours at ambient temperature. After concentration, the residue obtained is purified by chromatography on silica gel (eluant: petroleum ether/diethyl ether 1/2) to yield the expected product.

Step e: [7-({[4-(2-Pyridylamino)butanoyl]amino}methyl)-5H-benzo[a]cyclohepten-5-yl]acetic acid hydrochloride The expected product is obtained in accordance with the procedure described in Example 8, Step c, using as starting material the compound described in the above Step, and with the replacement of trifluoroacetic acid with an ethereal HCl solution.

Elemental microanalysis: $C_{23}H_{25}N_3O_3 \cdot HCl$

|  | C | H | N | Cl |
|---|---|---|---|---|
| % Calculated: | 64.01 | 6.10 | 9.74 | 9.04 |
| % Found: | 63.67 | 6.02 | 9.43 | 8.42 |

EXAMPLE 16

[7-({[5-(2-Pyridylamino)pentanoyl]amino}methyl)-5H-benzo-[a]cyclohepten-5-yl]acetic acid hydrochloride The expected product is obtained in accordance with the procedure described in Example 15 with the replacement, in Step d, of the product of Preparation F with the product of Preparation G.

EXAMPLE 17

[7-({[4-(3,4,5,6-tetrahydro-2H-azepin-7-ylamino) butanoyl]-amino}methyl)-5H-benzo[a]cyclohepten-5-yl]acetic acid trifluoroacetate The expected product is obtained in accordance with the procedure described in Step b of Example 8, using as starting material the compound described in Step c of Example 15 and with the replacement of the product of Preparation A with the compound described in Preparation P, followed by deprotection in accordance with Step c of Example 8.

EXAMPLE 18

[7-({[5-(3,4,5,6-Tetrahydro-2H-azepein-7-ylamino) pentanoyl]-amino}methyl)-5H-benzo[a]cyclohepten-5-yl]acetic acid trifluoroacetate The expected product is obtained in accordance with the procedure described in Step b of Example 8, using as starting material the compound described in Step c of Example 15 and with the replacement of the product of Preparation A with the compound described in Preparation T, followed by deprotection in accordance with Step c of Example 8.

EXAMPLE 19

[7-({[4-(4,5-Dihydro-1H-imidazol-2-ylamino) butanoyl]amino}-methyl)-5H-benzo[a]cyclohepten-5-yl]acetic acid trifluoro-acetate The expected product is obtained in accordance with the procedure described in Step b of Example 8, using as starting material the compound described in Step c of Example 15 and with the replacement of the product of Preparation A with the compound described in Preparation R, followed by deprotection in accordance with Step c of Example 8.

EXAMPLE 20

[7-({[5-(4,5-Dihydro-1H-imidazol-2-ylamino) pentanoyl]-amino}methyl)-5H-benzo[a]cyclohepten-5-yl]acetic acid trifluoro-acetate The expected product is obtained in accordance with the procedure described in Step b of Example 8, using as starting material the compound described in Step c of Example 15 and with the replacement of the product of Preparation A with the compound described in Preparation V, followed by deprotection in accordance with Step c of Example 8.

EXAMPLE 21

[7-({[4-(1H-Benzimidazol-2-ylamino)butanoyl] amino}methyl)-5H-benzo[a]cyclohepten-5-yl]acetic acid hydrochloride The expected product is obtained in accordance with the procedure described in Example 15 with the replacement, in Step d, of the product of Preparation F with the product of Preparation Q.

Elemental microanalysis: $C_{25}H_{26}N_4O_3 \cdot HCl$

|  | C | H | N | Cl |
|---|---|---|---|---|
| % Calculated: | 64.30 | 5.83 | 12.00 | 7.59 |
| % Found: | 64.34 | 5.81 | 11.90 | 7.38 |

EXAMPLE 22

[7-({[5-(1H-Benzimidazol-2-ylamino)pentanoyl] amino}methyl)-5H-benzo[a]cyclohepten-5-yl]acetic acid trifluoroacetate The expected product is obtained in accordance with the procedure described in Example 15 with the replacement, in Step d, of the product of Preparation F with the product of Preparation U.

EXAMPLE 23

[7-({[3-(2-Pyridylamino)propanoyl]amino}methyl)-6,9-dihydro-5H-benzo[a]cyclohepten-5-yl]acetic acid trifluoroacetate Step a: tert-Butyl{7-[(1,3-dioxo-1,3-dihydro-2H-isoindol-2-yl)methyl]-6,9-dihydro-5H-benzo[a]cyclohepten-5-yl}acetate Potassium phthalimidate (2 g; 11.38 mmol) is added at ambient temperature to a solution of the compound described in Step b of Example 1 (2 g; 5.69 mmol) in 15 ml of dimethylformamide. After stirring for 24 hours, the reaction mixture is diluted with 250 ml of dichloromethane and washed with a saturated aqueous sodium chloride solution. After extraction, the organic phase is dried over magnesium sulphate, concentrated and purified by chromatography on silica gel (eluant: toluene/ethyl acetate, 95/5) to yield the expected product.

Step b: tert-Butyl[7-(aminomethyl)-6,9-dihydro-5H-benzo[a]cyclohepten-5-yl]acetate The compound described in the above Step (1.45 g; 3.47 mmol) is diluted under an argon atmosphere with 35 ml of dichloromethane. Hydrazine monohydrate (520 mg; 10.41 mmol; 510 µl) dissolved in 35 ml of methanol is added dropwise thereto. The reaction mixture is stirred for 24 hours at ambient temperature. The precipitate formed is filtered off and the filtrate is concentrated. The residue obtained is taken up in ether and washed with an aqueous 5% sodium carbonate solution. The organic phase is dried over magnesium sulphate, concentrated and purified by chromatography on silica gel (eluant: dichloromethane/ethanol/ammonium hydroxide 95/5/0.5) to yield the expected product.

Step c: tert-Butyl {7-[((3-[(tert-butoxycarbonyl)(2-pyridyl)amino]propanoyl}-amino)methyl]-6,9-dihydro-5H-benzo[a]cyclohepten-5-yl}acetate A solution of the compound described in Preparation E (260 mg; 0.56 mmol) in 3 ml of dichloromethane is added dropwise to a solution of the compound described in the above Step (160 mg; 0.53 mmol) in 1 ml of dichloromethane. The reaction mixture is stirred for 24 hours at ambient temperature. After concentration, the residue obtained is purified by chromatography on silica gel (eluant petroleum ether/diethyl ether 1/2) to yield the title product.

Step d: [7-({[3-(2-Pyridylamino)propanoyl]amino}methyl)-6,9-dihydro-5H-benzo[a]cyclohepten-5-yl]acetic acid trifluoroacetate The expected product is obtained in accordance with the procedure described in Example 8, Step c, using as starting material the compound described in the above Step.

Elemental microanalysis: $C_{22}H_{25}N_3O_3.C_2HF_3O_2$

|  | C | H | N |
|---|---|---|---|
| % Calculated: | 58.41 | 5.31 | 8.51 |
| % Found: | 58.45 | 5.31 | 8.24 |

EXAMPLE 24

[7-({[4-(2-Pyridylamino)butanoyl]amino}methyl)-6,9-dihydro-5H-benzo[a]cyclohepten-5-yl]acetic acid hydrochloride The expected product is obtained in accordance with the procedure described in Example 23 with the replacement, in Step c, of the compound described in Preparation E with the compound described in Preparation F, and with the replacement, in Step d, of trifluoroacetic acid with an ethereal HCl solution. Chiral resolution on HPLC (eluant: n-heptane/EtOH/Et₃N 750/250/1)on a Whelk 01 chiral phase allows the 2 enantiomers to be obtained.

24a) (+) Elemental microanalysis: $C_{23}H_{27}N_3O_3.1.5HCl$

|  | C | H | N | Cl |
|---|---|---|---|---|
| % Calculated: | 61.63 | 6.42 | 9.38 | 11.86 |
| % Found: | 61.60 | 6.33 | 9.23 | 11.04 |

24b) (−) Elemental microanalysis: $C_{23}H_{27}N_3O_3.HCl$

|  | C | H | N | Cl |
|---|---|---|---|---|
| % Calculated: | 64.25 | 6.56 | 9.77 | 8.25 |
| % Found: | 64.14 | 6.17 | 9.55 | 9.18 |

EXAMPLE 25

[7-({[5-(2-Pyridylamino)pentanoyl]amino}methyl)-6,9-dihydro-5H-benzo[a]cyclohepten-5-yl]acetic acid hydrochloride The expected product is obtained in accordance with the procedure described in Example 23 with the replacement, in Step c, of the compound described in Preparation E with the compound of Preparation G, and with the replacement, in Step d, of trifluoroacetic acid with an ethereal HCl solution.

Elemental microanalysis: $C_{24}H_{29}N_3O_3.2HCl$

|  | C | H | N | Cl |
|---|---|---|---|---|
| % Calculated: | 60.00 | 6.50 | 8.75 | 14.76 |
| % Found: | 59.68 | 6.51 | 8.61 | 14.15 |

EXAMPLE 26 tert-Butyl{7-[({3-[(2-pyridylamino)methyl]benzoyl}amino)-methyl]-6,9-dihydro-5H-benzo[a]cyclohepten-5-yl}acetate The expected product is obtained in accordance with the procedure described in Example 23, Steps a, b and c with the replacement, in Step c, of the compound described in Preparation E with the compound of Preparation H.

EXAMPLE 27

{7-[({3-[(2-Pyridylamino)methyl]benzoyl}amino)methyl]-6,9-dihydro-5H-benzo[a]cyclohepten-5-yl}acetic acid trifluoroacetate The expected product is obtained in accordance with the procedure described in Example 8, Step c, using as starting material the compound described in Example 26.

Elemental microanalysis: $C_{27}H_{27}N_3O_3.C_2HF_3O_2$ (1.3 mol)

|  | C | H | N |
|---|---|---|---|
| % Calculated: | 60.28 | 4.85 | 7.13 |
| % Found: | 61.53 | 5.07 | 7.15 |

EXAMPLE 28

[7-({[4-(1H-Benzoimidazol-2-ylamino)butanoyl]amino}-methyl)-6,9-dihydro-5H-benzo[a]cyclohepten-5-yl]acetic acid hydrochloride The expected product is obtained in accordance with the procedure described in Example 23 with the replacement, in Step c, of the compound described in Preparation E with the compound of Preparation Q, and with the replacement, in Step d, of trifluoroacetic acid with an ethereal HCl solution.

Elemental microanalysis: $C_{25}H_{28}N_4O_3 \cdot HCl$

|  | C | H | N | Cl |
|---|---|---|---|---|
| % Calculated: | 64.03 | 6.23 | 11.95 | 7.56 |
| % Found: | 63.66 | 6.29 | 11.82 | 7.72 |

EXAMPLE 29 tert-Butyl [7-({[4-(N1-4,5,6,7-tetrahydro-3H-azepin-2-ylamino)-butanoyl]amino}methyl)-6,9-dihydro-5H-benzo[a]cyclohepten-5-yl]acetate The expected product is obtained in accordance with the procedure described in Step b of Example 8, with the replacement of the compound described in Preparation A with the compound of Preparation P, and with the replacement of the compound of Step a with the compound of Step b of Example 23.

EXAMPLE 30

[7-({[4-(N1-4,5,6,7-Tetrahydro-3H-azepin-2-ylamino)-butanoyl]-amino}methyl)-6,9-dihydro-5H-benzo[a]cyclohepten-5-yl]acetic acid hydrochloride The expected product is obtained in accordance with the procedure described in Example 8, Step c, using as starting material the compound described in Example 29, and with the replacement of trifluoroacetic acid with an ethereal HCl solution.

EXAMPLE 31 tert-Butyl [7-({[4-(4,5-dihydro-1H-imidazol-2-ylamino)-butanoyl]amino}methyl)-6,9-dihydro-5H-benzo[a]cyclohepten-5-yl]acetate The compound of Preparation X (9.66 mmol), the $Et_3N$ (1.14 g; 11.27 mmol; 1.61 ml), are added in succession at ambient temperature, with stirring, to a solution of the compound obtained in Preparation 5 (0.6 g; 1.61 mmol) in 9 ml of $CH_2Cl_2$. The reaction mixture is then heated at 35° C. for 72 hours. After returning to ambient temperature, the reaction mixture is hydrolysed and extracted with dichloromethane. After concentration of the organic phase, the residue obtained is chromatographed on silica gel (eluant: $CH_2Cl$/EtOH/$NH_4OH$ 98/2/0.2) to yield the title product.

EXAMPLE 32

[7-({[4-(4,5-Dihydro-1H-imidazol-2-ylamino) butanoyl]amino}-methyl)-6,9-dihydro-5H-benzo[a] cyclohepten-5-yl]acetic acid hydrochloride The procedure is as in Step d of Example 23, using ethereal HCl instead of trifluoroacetic acid.

Elemental microanalysis: $C_{21}H_{28}N_4O_3 \cdot 1.25HCl$

|  | C | H | N | Cl |
|---|---|---|---|---|
| % Calculated: | 54.75 | 7.40 | 12.17 | 9.69 |
| % Found: | 55.80 | 6.87 | 12.04 | 9.27 |

EXAMPLE 33 tert-Butyl {7-[({3-[(1,4,5,6-tetrahydro-2-pyrimidinylamino)-methyl)benzoyl}amino)methyl]-6,9-dihydro-5H-benzo[a]cyclohepten-5-yl}acetate The expected product is obtained in accordance with the procedure described in Example 8, Step b with the replacement of the compound described in Preparation A with the compound of Preparation S.

EXAMPLE 34

{7-[({3-[(1,4,5,6-Tetrahydro-2-pyrimidinylamino) methyl)-benzoyl}amino)methyl]-6,9-dihydro-5H-benzo[a]cyclohepten-5-yl}acetic acid trifluoroacetate The expected product is obtained in accordance with the procedure described in Example 8, Step c, using as starting material the compound described in Example 33.

EXAMPLE 35 tert-Butyl [2-oxo-3-(2-oxo-2-{[3-(2-pyridylamino) propyl]-amino}ethyl)-2,3,4,5-tetrahydro-1H-3-benzazepin-1-yl]acetate The expected product is obtained in accordance with the procedure described in Example 8 using as starting material in Step a the compound described in Preparation 3.

EXAMPLE 36

[2-Oxo-3-(2-x-2-{[3-(2-pyridylamino)propyl] amino}ethyl)-2,3,4,5-tetrahydro-1H-3-benzazepin-1-yl]acetic acid trifluoroacetate The expected product is obtained in accordance with the procedure described in Example 8, Step c, using as starting material the compound described in Example 35.

EXAMPLE 37 tert-Butyl [2-oxo-3-(2-oxo-2-{[4-(2-pyridylamino) butyl]-amino}ethyl)-2,3,4,5-tetrahydro-1H-3-benzazepin-1-yl]acetate The expected product is obtained in accordance with the procedure described in Example 8, using as starting material in Step a the compound described in Preparation 3 and with the replacement, in Step b, of the product of Preparation A with the product described in Preparation B.

EXAMPLE 38

[2-Oxo-3-(2-oxo-2-{[4-(2-pyridylamino)butyl] amino}ethyl)-2,3,4,5-tetrahydro-1H -3-benzazepin-1-yl]acetic acid trifluoroacetate The expected product is obtained in accordance with the procedure described in Example 8, Step c, using as starting material the compound described in Example 37.

EXAMPLE 39 tert-Butyl [2-oxo-3-(2-oxo-2-{[2-(2-pyridylamino)
ethyl]amino}-ethyl)-2,3,4,5-tetrahydro-1H-3-
benzazepin-1-yl]acetate The expected product is obtained in accordance with the procedure described in Example 8, using as starting material in Step a the compound described in Preparation 3 and with the replacement, in Step b, of the product of Preparation A with the product described in Preparation C.

EXAMPLE 40

[2-Oxo-3-(2-oxo-2-{[2-(2-pyridylamino)ethyl]
amino}ethyl)-2,3,4,5-tetrahydro-1H-3-benzazepin-1-
yl]acetic acid trifluoroacetate The expected product is obtained in accordance with the procedure described in Example 8, Step c, using as starting material the compound described in Example 39.

EXAMPLE 41 tert-Butyl {2-oxo-3-[2-oxo-2-({3-[(2-pyridylamino)
methyl]-benzyl}amino)ethyl]-2,3,4,5-tetrahydro-1H-
3-benzazepin-1-yl}acetate The expected product is obtained in accordance with the procedure described in Example 8, using as starting material in Step a the compound described in Preparation 3 and with the replacement, in Step b, of the product of Preparation A with the product described in Preparation D.

EXAMPLE 42

{2-Oxo-3-[2-oxo-2-({3-[(2-pyridylamino)methyl]
benzyl}amino)-ethyl]-2,3,4,5-tetrahydro-1H-3-
benzazepin-1-yl}acetic acid trifluoroacetate The expected product is obtained with the procedure described in Example 8, Step c, using as starting material the compound described in Example 41.

EXAMPLE 43 tert-Butyl [2-oxo-3-(2-oxo-2-{[3-(N1-4,5,6,7-
tetrahydro-3H-azepin-2-yl)propyl]amino}ethyl)-2,3,
4,5-tetrahydro-1H-3-benzazepin-1-yl]acetate The expected product is obtained in accordance with the procedure described in Example 8, using as starting material in Step a the compound described in Preparation 3 and with the replacement, in Step b, of the Preparation A with the product described in Preparation M.

EXAMPLE 44

[2-Oxo-3-(2-oxo-2-{[3-(N1-4,5,6,7-tetrahydro-3H-
azepin-2-yl)-propyl]amino}ethyl)-2,3,4,5-tetrahydro-
1H-3-benzazepin-1-yl]-acetic acid trifluoroacetate The expected product is obtained in accordance with the procedure described in Example 8, Step c, using as starting material the compound described in Example 43.

EXAMPLE 45 tert-Butyl [2-oxo-3-(2-oxo-2-{[3-(4,5-dihydro-1H-
imidazo-2-yl)-propyl]amino}ethyl)-2,3,4,5-
tetrahydro-1H-3-benzazepin-1-yl]acetate The expected product is obtained in accordance with the procedure described in Example 8, using as starting material in Step a the compound described in Preparation 3 and with the replacement, in Step b, of the product of Preparation A with the product described in Preparation N.

EXAMPLE 46

[2-Oxo-3-(2-oxo-2-{[3-(4,5-dihydro-1H-imidazo-2-
yl)propyl]-amino}ethyl)-2,3,4,5-tetrahydro-1H-3-
benzazepin-1-yl]-acetic acid trifluoroacetate The expected product is obtained in accordance with the procedure described in Example 8, Step c, using as starting material the compound described in Example 45.

EXAMPLE 47 tert-Butyl {2-oxo-3-[2-oxo-2-({3-[(4,5-dihydro-1H-
imidazo-2-ylamino)methyl]benzyl}amino)ethyl]-2,3,
4,5-tetrahydro-1H-3-benzazepin-1-yl}-acetate The expected product is obtained in accordance with the procedure described in Example 8, using as starting material in Step a the compound described in Preparation 3 and with the replacement, in Step b, of the product of Preparation A with the product described in Preparation O.

EXAMPLE 48

{2-Oxo-3-[2-oxo-2-({3-(4,5-dihydro-1H-imidazo-2-
ylamino)-methyl]benzyl}amino)ethyl]-2,3,4,5-
tetrahydro-1H-3-benzazepin-1-yl}acetic acid
trifluoroacetate The expected product is obtained in accordance with the procedure described in Example 8, Step c, using as starting material the compound described in Example 47.

EXAMPLE 49 tert-Butyl [7-({[4-(1,4,5,6-tetrahydro-2-
pyrimidinylamino)-butanoyl]amino}methyl)-6,9-
dihydro-5H-benzo[a]cyclohepten-5-yl]-acetate The compound of Preparation W (2.22 g; 9.66 mmol), then Et$_3$N (1.14 g; 11.27 mmol); 1.61 ml), are added in succession, with stirring, to a solution of the compound obtained in Preparation 5 (0.6 g; 1.16 mmol) in 9 ml of CH$_2$Cl$_2$ at ambient temperature. The reaction mixture is then heated at 35° C. for 72 hours. After returning to ambient temperature, the reaction mixture is hydrolysed and extracted with dichloromethane. After concentration of the organic phase, the residue obtained is chromatographed on silica gel (eluant: CH$_2$Cl$_2$/EtOH/NH$_4$OH 98/2/0.2) to yield the expected product in the form of a whitish mousse.

EXAMPLE 50

[7-({[4-(1,4,5,6-Tetrahydro-2-pyrimidinylamino)
butanoyl]-amino}methyl)-6,9-dihydro-5H-benzo[a]
cyclohepten-5-yl]-acetic acid hydrochloride The procedure is as in Step d of Example 23, using an ethereal HCl solution instead of trifluoroacetic acid.

Elemental microanalysis: $C_{22}H_{30}N_4O_3 \cdot HCl$

|  | C | H | N | Cl |
|---|---|---|---|---|
| % Calculated: | 60.75 | 7.18 | 12.88 | 8.15 |
| % Found: | 61.02 | 7.07 | 12.65 | 8.38 |

EXAMPLE 51 tert-Butyl {7-[({4-[(5-methoxy-1H-benzimidazol-2-yl)amino]-butanoyl}amino)methyl]-6,9-dihydro-5H-benzo[a]cyclohepten-5-yl}acetate With stirring under an argon atmosphere at −78° C., the compound of Preparation Y (1.274 g; 33.5 mmol), triethylamine (0.814 g; 8.05 mmol; 1.15 ml) and $HgCl_2$ (0.914 g; 3.36 mmol) are added in succession to a solution of the compound obtained in Preparation 5 (0.6 g; 16.1 mmol) in 10 ml of $CH_2Cl_2$. After stirring for 10 minutes at −78° C., the reaction mixture is filtered over Celite, washed with a saturated aqueous NaCl solution and extracted with dichloromethane. After drying and concentration of the organic phase, the residue obtained is chromatographed on silica gel (eluant: $CH_2Cl_2$/EtOH/$NH_4OH$ 98/2/0.2) to yield the desired compound in the form of a beige mousse.

EXAMPLE 52

{7-[({4-[(5-Methoxy-1H-benzimidazol-2-yl)amino]butanoyl}-amino)methyl]-6,9-dihydro-5H-benzo[a]cyclohepten-5-yl}-acetic acid hydrochloride The procedure is as in Step d of Example 23, with the replacement of trifluoroacetic acid with ethereal HCl.

Elemental microanalysis: $C_{26}H_{30}N_4O_4 \cdot HCl$

|  | C | H | N | Cl |
|---|---|---|---|---|
| % Calculated: | 62.58 | 6.29 | 11.23 | 7.10 |
| % Found: | 61.96 | 6.09 | 11.03 | 7.69 |

EXAMPLE 53 tert-Butyl {7-[({3-[(2-pyridylmethyl)amino]propanoyl}-amino)methyl]-6,9-dihydro-5H-benzo[a]cyclohepten-5-yl}acetate The procedure is as in Step c of Example 23, with the replacement of the compound obtained in Preparation E with the compound obtained in Preparation Z.

EXAMPLE 54

{7-[({3-[(2-Pyridylmethyl)amino]propanoyl}amino)methyl]-6,9-dihydro-5H-benzo[a]cyclohepten-5-yl}acetic acid hydrochloride The procedure is as in Step c of Example 8, starting from the compound obtained in Example 53.

EXAMPLE 55 tert-Butyl {7-[({3-[1H-benzimidazol-2-ylmethyl)amino]-propanoyl}amino)methyl]-6,9-dihydro-5H-benzo[a]cyclohepten-5-yl}acetate The procedure is as in Step c of Example 23, with the replacement of the compound obtained in Preparation E with the compound obtained in Preparation A1.

EXAMPLE 56

{7-[({3-[(1H-Benzimidazol-2-ylmethyl)amino]propanoyl}-amino)methyl]-6,9-dihydro-5H-benzo[a]cyclohepten-5-yl}-acetic acid hydrochloride The procedure is as in Step d of Example 23 starting from the compound obtained in Example 55, with the replacement of trifluoroacetic acid with ethereal HCl.

Elemental microanalysis: $C_{25}H_{28}N_4O_3 \cdot 2HCl$

|  | C | H | N | Cl |
|---|---|---|---|---|
| % Calculated: | 59.41 | 5.98 | 11.08 | 14.03 |
| % Found: | 59.64 | 5.93 | 10.95 | 14.27 |

EXAMPLE 57 tert-Butyl [7-({[4-(5,6,7,8-tetrahydro[1,8]naphthyridin-2-yl)butanoyl]amino}methyl)-6,9-dihydro-5H-benzo[a]cyclohepten-5-yl]acetate The procedure is as in Step b of Example 8, starting from the compound obtained in Step b of Example 23 and the compound obtained in Preparation $A_2$.

EXAMPLE 58

[7-({[4-(5,6,7,8-Tetrahydro[1,8]naphthyridin-2-yl)butanoyl]-amino}methyl)-6,9-dihydro-5H-benzo[a]cyclohepten-5-yl]acetic acid hydrochloride The compound obtained in Example 57 is dissolved in a $CH_2Cl_2$/ethereal HCl mixture and stirred at ambient temperature for 72 hours. The precipitate obtained is suction-filtered off to yield the title product.

Elemental microanalysis: $C_{26}H_{31}N_3O_3 \cdot 1.2HCl$

|  | C | H | N | Cl |
|---|---|---|---|---|
| % Calculated: | 65.42 | 6.81 | 8.81 | 8.91 |
| % Found: | 64.93 | 6.40 | 8.76 | 7.83 |

EXAMPLE 59 tert-Butyl [7-({[4-oxo-4-(2-pyridylamino)butanoyl]amino}-methyl)-6,9-dihydro-5H-benzo[a]cyclohepten-5-yl]acetate The compound obtained in Preparation $A_3$ (0.2 g; 1.12 mmol), diisopropylethylamine (0.724 g; 5.6 mmol; 0.97 ml) HOBT (1.34 mmol) and finally EDC (0.257 g; 1.34 mmol) are added in succession at ambient temperature, with stirring, to a solution of the compound obtained in Step b of Example 23 (0.322 g; 1.12 mmol) in 25 ml of $CH_2Cl_2$. The reaction mixture is stirred for 10 hours at ambient temperature and then concentrated to dryness, taken up in ethyl acetate, washed with a saturated aqueous $NH_4Cl$ solution and extracted with ethyl acetate. After drying and concentration of the organic phase, the residue obtained is purified by chromatography on silica gel (eluant: $CH_2Cl_2$/MeOH 98/2) to yield the title compound in the form of a viscous oil.

EXAMPLE 60

[7-({[4-Oxo-4-(2-pyridylamino)butanoyl]amino}methyl)-6,9-dihydro-5H-benzo[a]cyclohepten-5-yl]acetic acid hydrochloride The compound obtained in Step a is dissolved in 10 ml of $CH_2Cl_2$ and stirred in the presence of 25 ml of ethereal HCl at ambient temperature for 72 hours. The precipitate obtained is suction-filtered off to yield the title product in the form of a white powder.

EXAMPLE 61 tert-Butyl [7-({[4-(1,3-thiazol-2-ylamino)butanoyl]amino}-methyl)-6,9-dihydro-5H-benzo[a]cyclohepten-5-yl}acetate The procedure is as in Example 23, Step c, with the replacement of the compound obtained in Preparation E with the compound obtained in Preparation $A_4$.

EXAMPLE 62

[7-({[4-(1,3-Thiazol-2-ylamino)butanoyl]amino}methyl)-6,9-dihydro-5H-benzo[a]cyclohepten-5-yl]acetic acid hydrochloride The procedure is as in Step d of Example 23 starting from the compound obtained in Example 61, with the replacement of trifluoroacetic acid with ethereal HCl.

| Elemental microanalysis: $C_{21}H_{25}N_3O_3S.HCl$ | | | | |
|---|---|---|---|---|
| C | H | N | S | Cl |
| % Calculated: 56.90 | 5.97 | 9.48 | 7.23 | 9.60 |
| % Found: 56.85 | 5.90 | 9.26 | 7.13 | 9.19 |

EXAMPLE 63

Methyl [4-({[4-(2-pyridylamino)butanoyl]amino}methyl)-2,3-dihydro-1H-1-benzazepin-2-yl]acetate The title product is obtained in accordance with the procedure described in Steps c and d of Example 23, with the replacement of the compound described in Preparation E with the compound described in Preparation F and with the replacement of the compound of Step b with the compound obtained in Preparation 6, and then by carrying out the hydrolysis of NBoc in ethereal HCl instead of trifluoroacetic acid in Step d.

EXAMPLE 64

[4-({[4-(2-Pyridylamino)butanoyl]amino}methyl)-2,3-dihydro-1H-1-benzazepin-2-yl]acetic acid The compound obtained in Example 63 is subjected to the hydrolysis conditions LiOH/dioxane/$H_2O$ then HCl (1 N), described in Step a of Example 8.

EXAMPLE 65

Methyl [4-({[4-(4,5-dihydro-1H-imidazol-2-ylamino)butanoyl]-amino}methyl)-2,3-dihydro-1H-1-benzazepin-2-yl]acetate The expected product is obtained in accordance with the procedure described in Steps c and d of Example 23, with the replacement of the compound described in Preparation E with the compound of Preparation Q and of the starting compound of Step d with the compound obtained in Preparation 6, and by carrying out the hydrolysis of NBoc in ethereal HCl medium instead of trifluoroacetic acid in Step d.

EXAMPLE 66

[4-({[4-(4,5-Dihydro-1H-imidazol-2-ylamino)butanoyl]amino}-methyl)-2,3-dihydro-1H-1-benzazepin-2-yl]acetic acid The title product is obtained by subjecting the compound of Example 65 to the hydrolysis conditions LiOH/dioxane/$H_2O$ then HCl (1 N), described in Step a of Example 8.

Pharmacological Study

EXAMPLE A

Measurement of the in vitro Affinity to $\alpha_v\beta_3$ and $\alpha_v\beta_5$ Receptors of Vitronectin and to the $\alpha_{IIb}\beta_3$ Receptor of Fibrinogen Integrins purified by affinity chromatography starting from human placenta ($\alpha_v\beta_3$ and $\alpha_v\beta_5$, are diluted to a concentration of 500 ng/ml in a Tris buffer containing 2 mM $CaCl_2$ and 1 mM $MgCl_2$ and $MnCl_2$, pH 7.5 (binding buffer), and then transferred into Costar 96-well plates for one hour at ambient temperature, in an amount of 100 μl per well, to allow their absorption. After washing and blocking non-specific adhesion sites with bovine serum albumin, the absorbed integrins are incubated in the binding buffer containing 0.1% albumin, in the presence of absence of the compounds tested, with vitronectin (50 ng per well) or fibrinogen (1 μl per well) labelled with biotin. After washing the wells, the amount of vitronectin bound to the $\alpha_v\beta_3$ or $\alpha_v\beta_5$ integrin or the amount of fibrinogen bound to the $\alpha_{IIb}\beta_3$ integrin is evaluated indirectly, by recognition with an antibody directed against biotin and coupled with alkaline phosphatase, enabling detection by colorimetric reaction at 405 nm with para-nitrophenyl phosphate. The concentration of the compound resulting in 50% inhibition of the binding of the biotinyl ligand to integrin is then calculated ($IC_{50}$).
Results It appears that the compounds of the invention have $IC_{50}$s of the nanomolar order for the $\alpha_v\beta_3$ and $\alpha_v\beta_5$ receptors and the micromolar order for the $\alpha_{IIb}\beta_3$ platelet integrin.

EXAMPLE B $\alpha_v\beta_3$- and $\alpha_v\beta_5$-Integrin-dependent Cell Adhesion Test Endothelial cells derived from the umbilical vein of human placenta are used to study $\alpha_v\beta_3$ integrin-dependent adhesion. The cells are used in primary culture or in a line established after immortalisation by transfection with SV40 T antigen (Biol. Cell, 1991, 73, 7–14, J. Cell Physiol. 1993, 157, 41–51). The human ovarian carcinoma line IGROV1 is used for the $\alpha_v\beta_5$ integrin-dependent adhesion.

Human vitronectin is diluted in a phosphate buffer to a final concentration of 5 μ/ml and transferred into a 60-well Terasaki plate for 90 minutes at 37° C., in an amount of 10 μl per well, to enable its adsorption. After washing and blocking the non-specific adhesion sites with bovine serum albumin, the cells are introduced in the form of a suspension into the wells. The cells were recovered beforehand, by trypsinisation in RPMI culture medium without serum containing 0.5% bovine serum albumin, and preincubated for 30 minutes on ice with the compounds tested. After adhesion at 37° C. in the Terasaki plate for a duration of 20 minutes (endothelial cells) or one hour (IGROV1 line), the wells are washed. The cells that have adhered are fixed with formaldehyde, stained with crystal violet and counted by image analysis over the entirety of the wells. The concentration of compound leading to 50% inhibition of adhesion of the cells to vitronectin is then calculated ($IC_{50}$).

Results

The compounds of the invention exhibit activities ($IC_{50}$s) of the order of some tens of nM and some hundreds of nM for $\alpha_v\beta_5$- and $\alpha_v\beta_3$-dependent adhesion, respectively.

EXAMPLE C

Platelet Aggregation Test

Venous blood from human donors who have not absorbed aspirin for the 15 preceding days is removed over 3.8% sodium citrate (one volume per nine volumes of blood). The blood samples are centrifuged for 15 minutes at 160 g. PRP (platelet-rich plasma) is collected and the platelets are counted. PPP (platelet-poor plasma) is then obtained by centrifuging the remaining blood for 15 minutes at 3000 g. The samples are tested on a 4-channel aggregometer, the PPP being used as a blank (100% transmission). 250 µl of PRP (0% transmission) are introduced into each microtube. Aggregation is induced by 10 µM ADP (2.5 µl per tube) and the aggregation curve is then obtained (% transmission relative to time). The products to be tested (2.5 µl) are added to the PRP at various concentrations three minutes prior to the addition of the aggregation agent. The results are expressed as a percentage inhibition of platelet aggregation.

Results

The compounds of the invention do not appear to have had an effect on platelet aggregation at doses up to 100 µM.

EXAMPLE D

Endothelial Cell Proliferation Test

Endothelial cells from human placenta umbilical vein are used in primary culture and inoculated into 96-well culture plates. After 24 hours' preculture in complete culture medium containing foetal calf serum, the cells are placed together with the compounds in the same medium for 96 hours. The cells are counted by an indirect colorimetric method. The concentration of compound leading to 50% inhibition of proliferation is then calculated ($IC_{50}$).

Results

It appears that the compounds of the invention have $IC_{50}$s of the order of from 10 to 100 nM for endothelial cells.

EXAMPLE E

Pharmaceutical Composition

| Formulation for the preparation of 1000 tablets each containing a dose of 10 mg | |
| --- | --- |
| compound of Example 24 | 10 g |
| hydroxypropyl cellulose | 2 g |
| wheat starch | 10 g |
| lactose | 100 g |
| magnesium stearate | 3 g |
| talc | 3 g |

What is claimed is:

1. A compound selected from those of formula (I): t,0250
wherein:

G represents a phenyl unsubstituted or substituted by $R_1$, $R_2$, $R_3$ and/or $R_4$, $G_1$ and $G_2$ independently represent a carbon, —$T_1$ represents a group selected from —CH=CH— and =CH—$CH_2$—, in which case —$T_2$— represents a bond, $R_1$, $R_2$, $R_3$ and $R_4$ independently represent halogen, alkyl, perhaloalkyl, cyano, nitro, $OR_7$, $NR_6R_{6'}$, $COOR_6$, $CONR_6R_{6'}$, $COR_6$ or $S(O)_nR_6$, wherein n is 0, 1 or 2, $R_5$ represents a —$(CH_2)_m$—$COOR_6$, $R_6$ and $R_{6'}$ independently represent hydrogen, alkyl, optionally substituted aryl, or optionally substituted arylalkyl, $R_7$ represents a hydrogen or an alkyl, —W— represents —CH—, =C— or —C= and —A— represents —$CH_2$—, =CH— or —CH=, —X— represents a group selected from —CO—$X_1$—, —CO—$NR_6$—$X_1$—, —$NR_6$—CO—$X_1$—, —O—$X_1$—, —$SO_2$—$NR_6$—$X_1$— and —$S(O)_n$—$X_1$—, wherein n is from 0 to 2 inclusive and $X_1$ represents an alkylene, —Y— represents a group selected from —$Y_1$—, —$Y_2$—$Y_1$—, and —$Y_1$—$Y_2$—$Y_1$—, wherein $Y_1$ represents alkylene, alkenylene, or alkynylene, and $Y_2$ represents arylene, heteroarylene, cycloalkylene, or heterocycloalkylene, Z— represents a group selected from $Z_1$—, $Z_1$—$NR_6$— and $Z_1$—$NR_6$—CO— wherein $Z_1$ represents a group selected from $Z_2$,

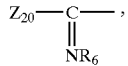

$Z_2$—$NR_6$— and $Z_2$—$NR_6$—, CO—, wherein $Z_2$ represents an optionally substituted heteroaryl, an optionally substituted heterocycloalkyl, an optionally substituted heteroarylalkyl, an optionally substituted heterocycloalkylalkyl, an optionally substituted fused arylheteroaryl, an optionally substituted fused arylheterocycloalkyl, an optionally substituted fused heteroarylheterocycloalkyl, an optionally substituted fused heterocycloalkylheteroayl, an optionally substituted fused heteroatylheteroaryl or a fused cycloalkylheterocycloalkyl, m is an integer of from 1 to 6 inclusive, wherein:

"alkyl" is a linear or branched, 1 to 6 carbon alkyl group,

"heteroalkyl" is an alkyl in which a carbon atom has been replaced by a hetero atom selected from nitrogen, oxygen and sulphur, "alkylene" is a linear or branched divalent 1 to 6 carbon group, "alkenylene" is a linear or branched divalent 2 to 6 carbon group with 1 to 3 double bonds, "alkynylene" is a linear or branched divalent 2 to 6 carbon group with 1 to 3 triple bonds, "cycloalkyl" is a saturated 3 to 8 carbon cyclic group, "cycloalkylene" is a saturated 3 to 8 carbon cyclic divalent group, "heterocycloalkyl" is a saturated cyclic 5 to 7 ring membered group with 1 to 3 hetero atoms selected from nitrogen, oxygen and sulphur, "aryl" is a phenyl or naphthyl, "heteroaryl" is an unsaturated or partially unsaturated mono- or bi-cyclic 5 to 11 membered group with 1 to 5 hereto atoms selected from nitrogen, oxygen and sulphur, "fused arylheteroaryl" is a polycyclic group formed by an aryl and a heteroaryl, each as defined hereinabove, and conjoined by means of any one of their bonds, "fused arylheterocycloalkyl" is a bi- or tri-cyclic group formed by an aryl and a heterocycloalkyl, each as defined hereinabove, and conjoined by means of any one of their bonds, "fused heteroarylheterocycloalkyl" is a bi- or tri-cyclic group formed by a heteroaryl and a heterocycloalkyl, each as defined hereinabove, and conjoined by means of any one of their bonds, "fused heterocycloalkylheteroaryl" is a bi- or tri-cyclic group formed by a heteroaryl and a heterocycloalkyl, each as defined hereinabove, and conjoined by means of any one of their bonds, "fused heteroarylheteroaryl" is a polycyclic group formed by two heteroaryl groups, as defined hereinabove, and conjoined by means of any one of their bonds, "fused cycloalkylheterocycloalkyl" is a bicyclic group formed by a cycloalkyl and a heterocycloalkyl, each as defined hereinabove, and conjoined by means of any one of their bonds, the ending "-ene" is that the group in question is a divalent radical having the same meanings as the base radical, the expression "optionally substituted" in connection with the groups heterocycloalkyl, aryl, arylalkyl, heteroaryl, fused arylheteroaryl, fused heteroarylheterocycloalkyl, fused heteroarylheteroaryl and fused arylheterocycloalkyl is that those groups are unsubstituted or substituted by one or more atoms or groups selected from alkyl, alkoxy, hydroxy mercapto, cyano, amino (optionally substituted by one or two alkyl), nitro, carboxy, alkoxycarbonyl, aminocarbonyl (optionally substituted by one or two alkyl), wherein the heteroaryl and heterocycloalkyl groups may also be substituted by an oxo, its enantiomers, diastereoisomers, and addition salts thereof with a pharmaceutically acceptable acid or base.

2. A compound of claim 1, wherein $R_5$ represents a —$CH_2$—$COOR_6$ group.

3. A compound of claim 1, wherein X is selected from —CO—$NR_6$—$X_1$, —$NR_6$—CO—$X_1$ and —O—$X_1$.

4. A compound of claim 1, wherein Y represents $Y_1$ or the group $Y_1$—$Y_2$—$Y_1$.

5. A compound of claim 1, wherein Z represents a heteroaryl, heterocycloalkyl, fused arylheteroaryl or fused heterocycloalkylheteroaryl.

6. A compound of claim 1, wherein Z represents $Z_{1[o]}$—$NR_6$.

7. A compound of claim 1, $R_5$ represents a —$CH_2$—$COOR_6$, $R_6$ is selected from hydrogen and alkyl, A represents —$CH_2$— or —CH= and W represents a —CH— or —C=.

8. A compound of claim 1, wherein X is selected from —CO—$NR_6$—$X_1$—, —$NR_6$—CO—$X_1$— and —O—$X_1$—, $X_1$ is methylene, Y represents —$Y_1$— or the group —$Y_1$—$Y_2$—$Y_1$— in which $Y_1$ is alkylene and $Y_2$ represents arylene, and Z represents heteroaryl, heterocycloalkyl, fused arylheteroaryl or fused heterocycloalkylheteroaryl or $Z_1$—$NR_6$, wherein $Z_1$ represents a group selected from heteroaryl, heterocycloalkyl, fused arylheteroaryl and fused heterocycloalkylheteroaryl, and $R_6$ is hydrogen.

9. A compound of claim 1, wherein X is selected from —CO—$NR_6$—$X_1$—, —$NR_6$—CO—$X_1$— and —O—$X_1$—, $X_1$ is methylene, Y represents —$Y_1$— or the group —$Y_1$—$Y_2$—$Y_1$— in which $Y_1$ is alkylene and $Y_2$ is arylene, and Z represents heteroaryl, heterocycloalkyl, fused arylheteroaryl or fused heterocycloalkylheteroaryl or $Z_1$—$NR_6$ wherein $Z_1$ represents a group selected from heteroaryl, heterocycloalkyl, fused arylheteroaryl and fused heterocycloalkylheteroaryl, and $R_6$ is hydrogen.

10. A compound of claim 1, wherein X is selected from —CO—$NR_6$—CO—$X_1$—, —$NR_6$—CO—$X_1$— and —O—$X_1$—, $X_1$ is methylene, Y represents —$Y_1$— or the group —$Y_1$—$Y_2$—$Y_1$ in which $Y_1$ is alkylene and $Y_2$ represents arylene, and Z represents heteroaryl, heterocycloalkyl, fused arylheteroaryl or fused heterocycloalkylheteroaryl or $Z_1$—$NR_6$, wherein $Z_1$ represents a group selected from heteroaryl, heterocycloalkyl, fused arylheteroaryl and fused heterocycloalkylheteroaryl, and $R_6$ is hydrogen.

11. A compound of claim 1, which is [7-({[4-(2-pyridylamino)butanoyl]amino}methyl)-6,9-dihydro-5H-benzo[a]cyclohepten-5-yl]acetic acid.

12. A compound of claim 1, which is [7-({[5-(2-pyridylamino)pentanoyl]amino}methyl)-6,9-dihydro-5H-benzo[a]cyclohepten-5-yl]acetic acid hydrochloride.

13. A compound of claim 1, which is [7-(2-oxo-2-{[3-(2-pyridylamino)propyl]amino}ethyl)-5H-benzo[a]cyclohepten-5-yl]acetic acid.

14. A compound of claim 1, which is [7-({[4-(4,5-dihydro-1H-imidazol-2-ylamino)butanoyl]amino}methyl)-6,9-dihydro-5H-benzo[a]cyclohepten-5-yl]acetic acid hydrochloride.

15. A compound of claim 1, which is [7-({[4-(2-pyridylamino)butanoyl]amino}methyl)-5H-benzo[a]cyclohepten-5-yl]acetic acid.

16. A compound of claim 1, which is [7-({[4-(1H-benzimidazol-2-ylamino)butanoyl]amino}methyl)-5H-benzo[a]cyclohepten-5-yl]acetic acid.

17. A compound of claim 1, which is [7-({[4-(1H-benzimidazol-2-ylamino)butanoyl]amino}methyl)-6,9-dihydro-5H-benzo[a]cyclohepten-5-yl]acetic acid.

18. A compound of claim 1, which is [7-({[4-(1,4,5,6-tetrahydro-2-pyrimidinylamino)butanoyl]amino}methyl)-6,9-dihydro-5H-benzo[a]cyclohepten-5-yl]acetic acid hydrochloride.

19. A compound of claim 1, which is [7-({[4-(5,6,7,8-tetrahydro[1,8]naphthyridin-2-yl)butanoyl]amino}methyl)-6,9-dihydro-5H-benzo[a]cyclohepten-5-yl]acetic acid hydrochloride.

20. A pharmaceutical composition comprising as active principle an effective amount of at least one compound of claim 1, alone or together with one or more pharmaceutically acceptable, excipients or carriers.

21. A method for treating a living body afflicted with a condition treatable by a vitronectin receptor antagonist, comprising the step of administering to the living body an amount of a compound of claim 1 which is effective for alleviation of the condition.

22. A method for treating a living body afflicted with a condition treatable by an inhibitor of tumour growth and of metastases formation, comprising the step of administering to the living body an amount of compound of claim 1 which is effective for alleviation of said condition.

23. The method of claim 21, wherein the condition treatable by a vitronectin receptor antagonist is cardiovascular disease, inflammatory disorders, cancer, osteoporosis, rheumatoid arthritis, psoriasis or retinopathy.

24. The method of claim 22, wherein the condition treatable by an inhibitor of tumour growth and metastases formation is cancer.

* * * * *

UNITED STATES PATENT AND TRADEMARK OFFICE
CERTIFICATE OF CORRECTION

PATENT NO. : 6,846,833 B2
DATED : January 25, 2005
INVENTOR(S) : Patrick Casara et al.

It is certified that error appears in the above-identified patent and that said Letters Patent is hereby corrected as shown below:

Title page,
Item [73], Assignee, "Les Laboratories Servier" should be -- Less Laboratoires Servier --.

Column 49,
Line 63, "t,0250" should be

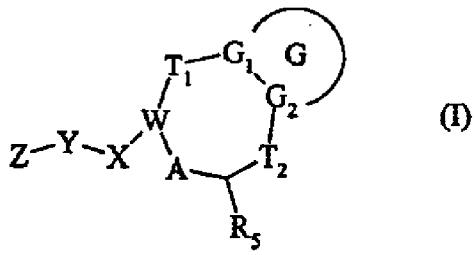

Signed and Sealed this

Twenty-fourth Day of May, 2005

JON W. DUDAS
*Director of the United States Patent and Trademark Office*